United States Patent
Wright et al.

(10) Patent No.: US 7,026,927 B2
(45) Date of Patent: Apr. 11, 2006

(54) RECEIVER USED IN MARKER LOCALIZATION SENSING SYSTEM AND HAVING DITHERING IN EXCITATION PULSES

(75) Inventors: J. Nelson Wright, Mercer Island, WA (US); Laurence J. Newell, Mercer Island, WA (US)

(73) Assignee: Calypso Medical Technologies, Inc., Seattle, WA (US)

( * ) Notice: Subject to any disclaimer, the term of this patent is extended or adjusted under 35 U.S.C. 154(b) by 135 days.

(21) Appl. No.: 10/750,453

(22) Filed: Dec. 31, 2003

(65) Prior Publication Data

US 2005/0151650 A1 Jul. 14, 2005

(51) Int. Cl.
*H04Q 7/00* (2006.01)
(52) U.S. Cl. .............. 340/539.12; 128/899; 600/12
(58) Field of Classification Search .......... 340/539.12, 340/539.11, 539.13, 286.07, 573.1, 572.1, 340/825.49, 10.1; 600/418, 409, 407, 12, 600/13, 14, 426; 128/899; 604/20, 362
See application file for complete search history.

(56) References Cited

U.S. PATENT DOCUMENTS

| | | | | |
|---|---|---|---|---|
| 5,057,095 | A * | 10/1991 | Fabian | 604/362 |
| 6,165,135 | A * | 12/2000 | Neff | 600/561 |
| 6,564,807 | B1 * | 5/2003 | Schulman et al. | 128/899 |
| 2002/0193685 | A1 * | 12/2002 | Mate et al. | 600/424 |
| 2003/0041866 | A1 * | 3/2003 | Linberg et al. | 128/899 |
| 2003/0066537 | A1 * | 4/2003 | Fabian et al. | 128/899 |
| 2003/0105394 | A1 * | 6/2003 | Fabian et al. | 600/407 |
| 2003/0122653 | A1 * | 7/2003 | Dimmer | 340/10.1 |
| 2003/0149353 | A1 * | 8/2003 | Boos | 600/407 |

* cited by examiner

Primary Examiner—Brent A. Swarthout
(74) Attorney, Agent, or Firm—Perkins Coie LLP

(57) ABSTRACT

A receiver for determining the location of a marker that is excited with an exciting waveform. A sensing array having coils is used to sense magnetic flux from the resonating marker. The coils provide inputs to the receiver. The receiver includes a correlation processor for analyzing the inputs in a coherent manner. Further, the exciting waveform is repeated with random dithering in order to eliminate system noise.

13 Claims, 15 Drawing Sheets

US 7,026,927 B2

RECEIVER USED IN MARKER LOCALIZATION SENSING SYSTEM AND HAVING DITHERING IN EXCITATION PULSES

CROSS-REFERENCE TO RELATED APPLICATIONS

This application is related to U.S. patent application Ser. No. 10/334,700 filed Dec. 30, 2002, U.S. patent application Ser. No. 10/382,123, filed Mar. 4, 2003, and U.S. patent application Ser. No. 10/679,801 filed Oct. 6, 2003 all of which are incorporated herein by reference in their entirety.

BACKGROUND

Implantable markers have been used to identify locations within objects, such as a human body. For example, a marker may be implanted in a patient within an organ of interest. As the patient moves, the marker can be used to track the location of the organ. Various techniques have been used to identify the location of such markers.

As described in my co-pending U.S. patent applications noted above, one technique for locating a marker is by measuring the magnetic flux generated by the marker upon excitation from a source. The measurement of the magnetic flux is typically performed by an array of sensing elements that together form a sensing array. In some sensing arrays, each of the sensing elements has their output coupled to their own dedicated amplifier circuit.

The signals from the sensing elements are then output to a receiver that is operative to extract the signal portion from the sensing elements from noise, which may be caused from various sources including the excitation from the source, co-channel or cross-channel interference between sensing elements, radiation sources in the examination environment, etc . . . .

The design of a receiver suitable for use with magnetic flux sensing systems has been problematic and challenging.

Sizes of various depicted elements are not necessarily drawn to scale, and these various elements may be arbitrarily enlarged to improve legibility. Also, the headings provided herein are for convenience only and do not necessarily affect the scope or meaning of the claimed invention.

DETAILED DESCRIPTION

The present invention provides a receiver apparatus that receives and processes input signals from a magnetic flux sensing array. In one embodiment, the sensing array includes multiple electromagnetic field sensors (also referred to as sensing elements) arranged in a locally planar array (e.g., an array in a common plane), and multiple sense signal output paths coupled to the sensors. The sensors and the corresponding output paths are configured to provide an output signal representing at least a portion of an electromagnetic field emitted by the marker; the output signal from a specific sensor is proportional to the component of the field that is substantially perpendicular to the plane of the sensor integrated over its aperture. Again, although one embodiment is described herein where the sensing array is substantially formed in a common plane, the methods and systems of the present invention may also be used with non-common plane sensing arrays.

The invention will now be described with respect to various embodiments. The following description provides specific details for a thorough understanding of, and enabling description for, these embodiments of the invention. However, one skilled in the art will understand that the invention may be practiced without these details. In other instances, well-known structures and functions have not been shown or described in detail to avoid unnecessarily obscuring the description of the embodiments of the invention.

Description of Suitable Systems

Figure 1:
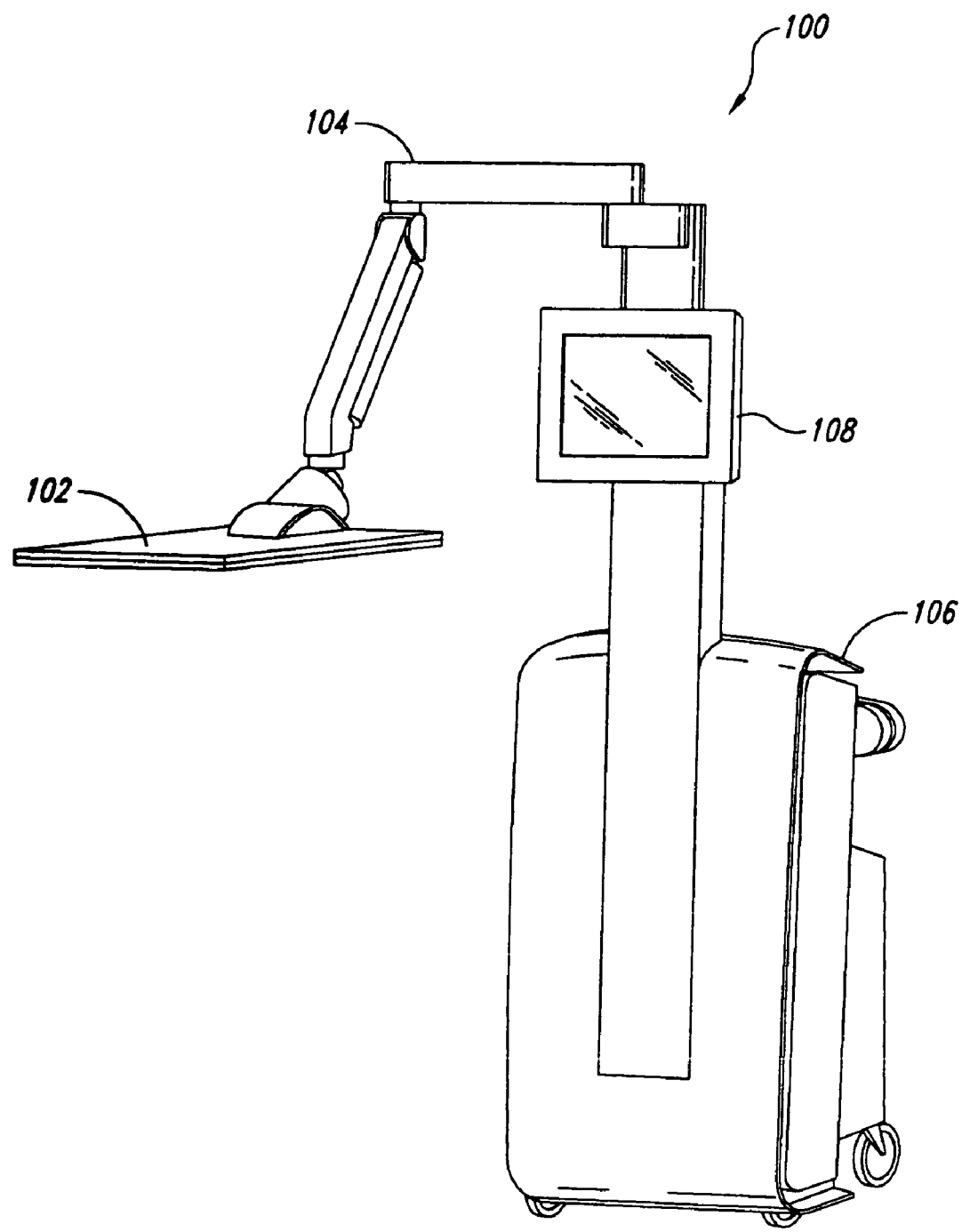
FIG. 1 is a perspective view of an example of a system for estimating the location of wireless implantable markers.

FIG. 1 is a perspective view showing an example of a system 100 for energizing and locating one or more wireless markers in three-dimensional space. The system includes an excitation source and sensor array 102 supported by a movable arm 104. The arm 104 is secured to a base unit 106 that includes various components, such as a power supply, computer (such as an industrial personal computer), and input and output devices, such as a display 108. Many of these components are described in detail below.

The system 100 may be used with guided radiation therapy to accurately locate and track a target in a body to which guided radiation therapy is delivered. Further details on use of the system with such therapy may be found in U.S. patent application Ser. No. 09/877,498, entitled "Guided Radiation Therapy System," filed Jun. 8, 2001, which is herein incorporated by reference. In general, a radiation source provides radiation for irradiating a tumor or other area of a patient or subject. Because of the toxic nature of the radiation, it is important to precisely and accurately focus the radiation onto the desired site. In accordance with the present invention, the system is operative to locate a marker implanted or attached (generically "associated") in or near the tumor, the marker acting as a guide point for the radiation therapy. In accordance with one aspect of the present invention, the system 100 is synchronized with the radiation source such that potentially interfering effects from the radiation source is not being applied during the locating process. In one embodiment, the locating process is interleaved in time with the potentially interfering operations of the radiation source (typically a linear accelerator).

Figure 2:
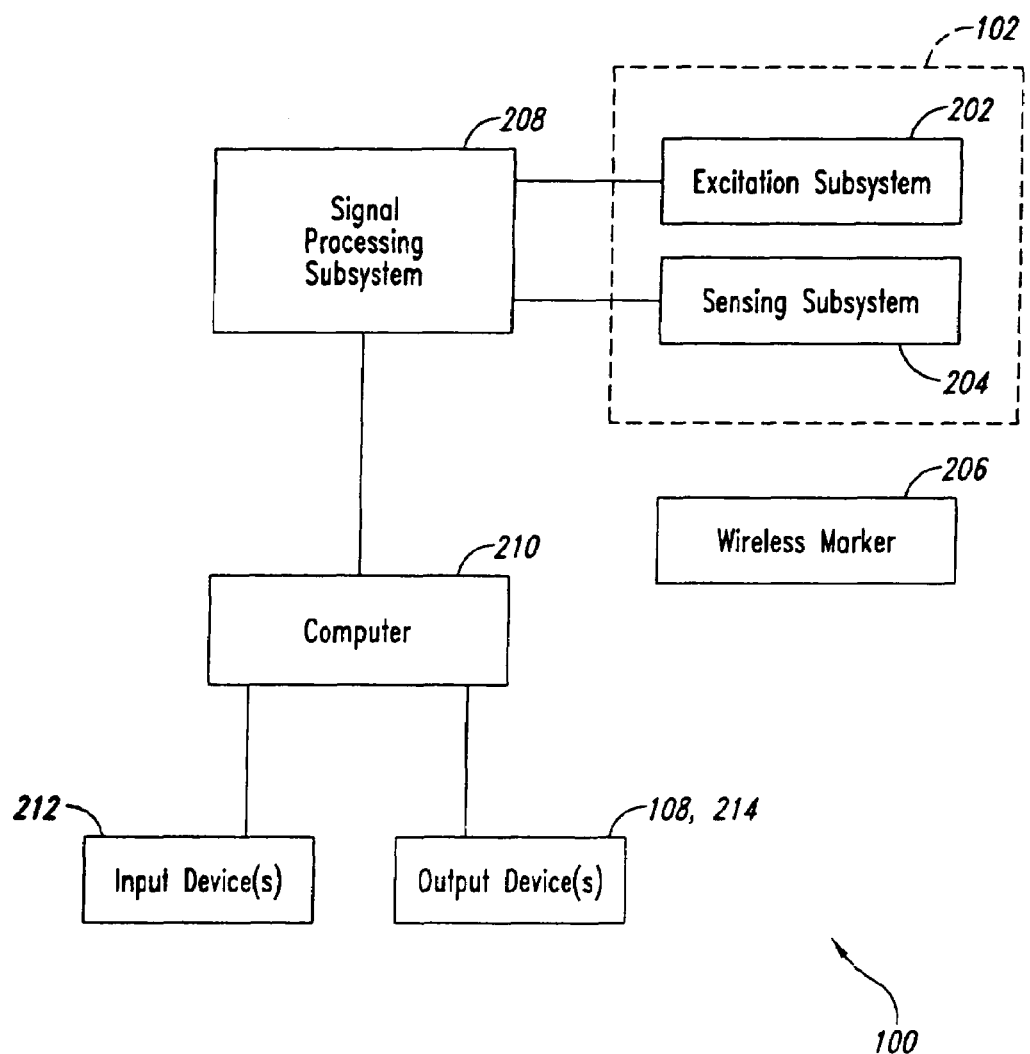
FIG. 2 is a block diagram illustrating components of the system of FIG. 1 including a sensing subsystem.

FIG. 2 is a block diagram of certain components of the system 100. In particular, the excitation source and sensor array 102 includes an excitation system 202 and a sensing subsystem 204. The excitation system 202 outputs electromagnetic energy to excite at least one wireless marker 206, and the sensing system 204 receives electromagnetic energy from the marker. Details regarding the sensing subsystem 204 are provided below.

A signal processing subsystem 208 provides signals to the excitation subsystem 202 to generate the excitation signals. In the embodiment depicted herein, excitation signals in the range of 300 to 500 kilohertz may be used. The signal processing subsystem 208 also receives signals from the sensing subsystem 204. The signal processing subsystem 208 filters, amplifies and correlates the signals received from the sensing subsystem 204 for use in a computer 210.

The computer 210 may be any suitable computer, such as an industrial personal computer suitable for medical applications or environments. One or more input devices 212 are coupled to the computer and receive user input. Examples of such input devices 212 include keyboards, microphones, mice/track balls, joy sticks, etc. The computer generates output signals provided to output devices 214. Examples of such output devices include the display device 108, as well as speakers, printers, and network interfaces or subsystems to connect the computer with other systems or devices.

Unless described otherwise herein, several aspects of the invention may be practiced with conventional systems. Thus, the construction and operation of certain blocks shown in FIG. 2 may be of conventional design, and such blocks need not be described in further detail to make and use the invention because they will be understood by those skilled in the relevant art.

Description of Suitable Sensing Subsystems

Figure 3A:
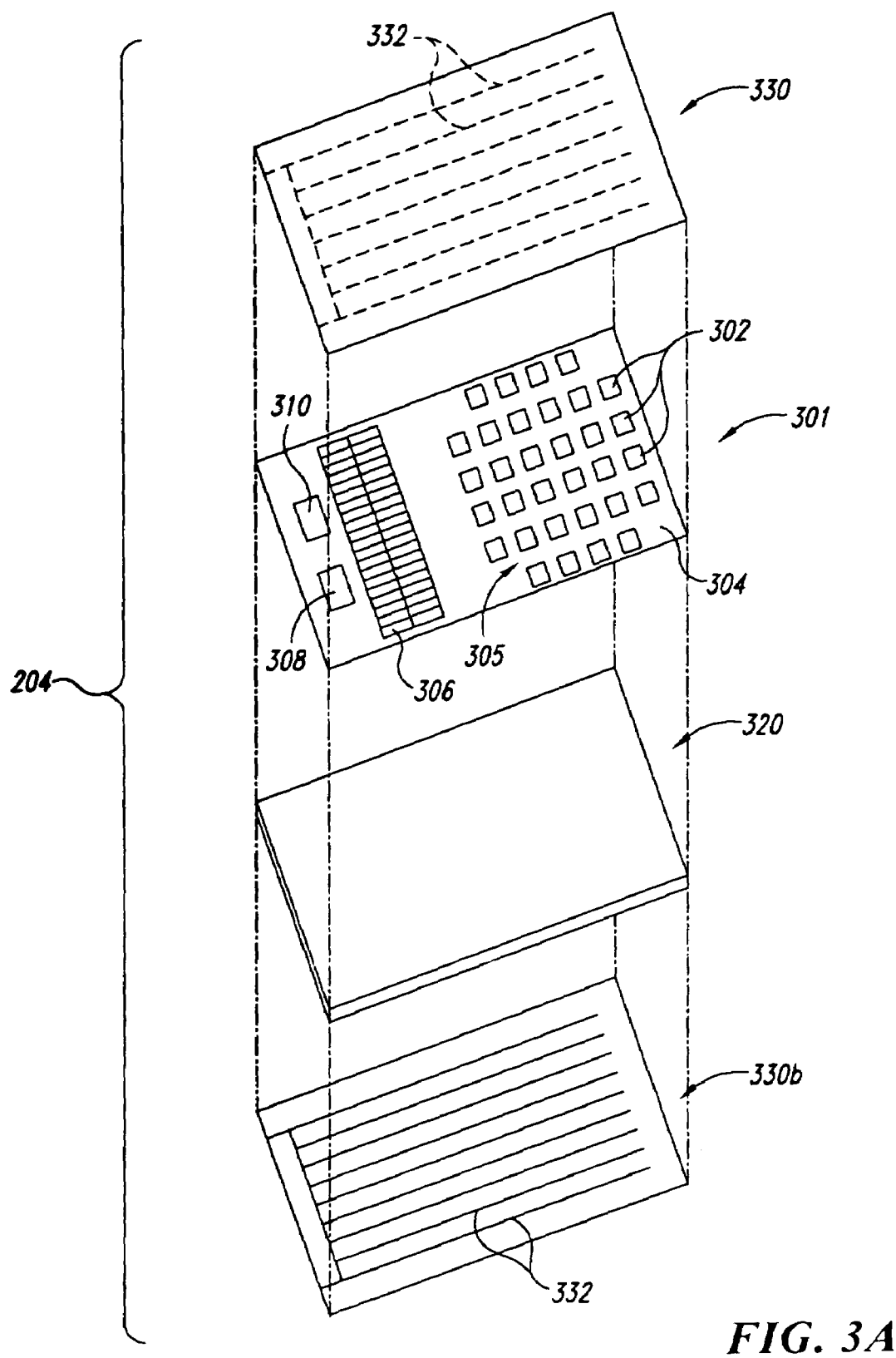
FIG. 3A is an exploded isometric view showing individual components of a sensing subsystem in accordance with an embodiment of the invention.

FIG. 3A is an exploded isometric view showing several components of the sensing subsystem 204. The subsystem 204 includes a sensing assembly 301 having a plurality of coils 302 formed on or carried by a panel 304. The coils are arranged in a sensor array 305. The panel 304 may be a substantially non-conductive sheet, such as KAPTON® produced by DuPont. KAPTON® is particularly useful when an extremely stable, tough, and thin film is required (such as to avoid radiation beam contamination), but the panel 304 may be made from other materials. For example, FR4 (epoxy-glass substrates), GETEK and Teflon-based substrates, and other commercially available materials can be used for the panel 304. Additionally, although the panel 304 may be a flat, highly planar structure, in other embodiments, the panel may be curved along at least one axis. In either embodiment, the panel is at least substantially locally planar such that the plane of one coil is at least substantially coplanar with the planes of adjacent coils. For example, the angle between the plane defined by one coil relative to the planes defined by adjacent coils can be from approximately 0° to 10°, and more generally is less than 5°. In some circumstances, however, one or more of the coils may be at an angle greater than 10° relative to other coils in the array.

The sensing subsystem 204 shown in FIG. 3A can further include a low-density foam spacer or core 320 laminated to the panel 304. The foam core 320 can be a closed-cell Rohacell foam. The foam core 320 is preferably a stable layer that has a low coefficient of thermal expansion so that the shape of the sensing subsystem 204 and the relative orientation between the coils 302 remains within a defined range over an operating temperature range.

The sensing subsystem 204 can further include a first exterior cover 330a on one side of the sensing subsystem and a second exterior cover 330b on an opposing side. The first and second exterior covers 330a–b can be thin, thermally stable layers, such as Kevlar or Thermount films. Each of the first and second exterior covers 330a–b can include electric shielding 332 to block undesirable external electric fields from reaching the coils 302. The electric shielding is configured to prevent or minimize the presence of eddy currents caused by the coils 302. The electric shielding can be a plurality of parallel legs of gold-plated, copper strips to define a comb-shaped shield in a configuration commonly called a Faraday shield. It will be appreciated that the shielding can be formed from other materials that are suitable for shielding. The electric shielding can be formed on the first and second exterior covers using printed circuit board manufacturing technology or other techniques.

The panel 304 with the coils 302 is laminated to the foam core 320 using an epoxy or another type of adhesive. The first and second exterior covers 330a–b are similarly laminated to the assembly of the panel 304 and the foam core 320. The laminated assembly forms a rigid, lightweight structure that fixedly retains the arrangement of the coils 302 in a defined configuration over a large operating temperature range. As such, the sensing subsystem 204 does not substantially deflect across its surface during operation. The sensing subsystem 204, for example, can retain the array of coils 302 in the fixed position with a deflection of no greater than ±0.5 mm, and in some cases no more than ±0.3 mm. The stiffness of the sensing subsystem 204 provides very accurate and repeatable monitoring of the precise location of leadless markers in real time.

The sensing subsystem 204 can also have a low mass per unit area in the plane of the sensor coils 302. The "mass-density" is defined by the mass in a square centimeter column through the thickness of the sensing subsystem 204 orthogonal to the panel 304. In several embodiments, the sensing subsystem 204 has a low-density in the region of the coils 302 to allow at least a portion of the sensing subsystem 204 to dwell in a radiation beam of a linear accelerator used for radiation oncology. For example, the portion of the sensing subsystem 204 including the coils 302 can have a mass density in the range of approximately $1.0^2$ gram/cm or less. In general, the portion of the sensing subsystem that is to reside in the beam of a linear accelerator has a mass-density between approximately 0.1 grams/cm$^2$ and 0.5 grams/cm$^2$, and often with an average mass-density of approximately 0.3 grams/cm$^2$. The sensing subsystem 204 can accordingly reside in a radiation beam of a linear accelerator without unduly attenuating or contaminating the beam. In one embodiment, the sensing subsystem 204 is configured to attenuate a radiation beam by approximately only 0.5% or less, and/or increase the skin dose in a patient by approximately 80%. In other embodiments, the panel assembly can increase the skin dose by approximately 50%. Several embodiments of the sensing subsystem 204 can accordingly dwell in a radiation beam of a linear accelerator without unduly affecting the patient or producing large artifacts in x-ray films.

In still another embodiment, the sensing subsystem 204 can further include a plurality of source coils that are a component of the excitation subsystem 202. One suitable array combining the sensing subsystem 204 with source coils is disclosed in U.S. patent application Ser. No. 10/334,700, entitled PANEL-TYPE SENSOR/SOURCE ARRAY ASSEMBLY, filed on Dec. 30, 2002, which is herein incorporated by reference.

Figure 3B:
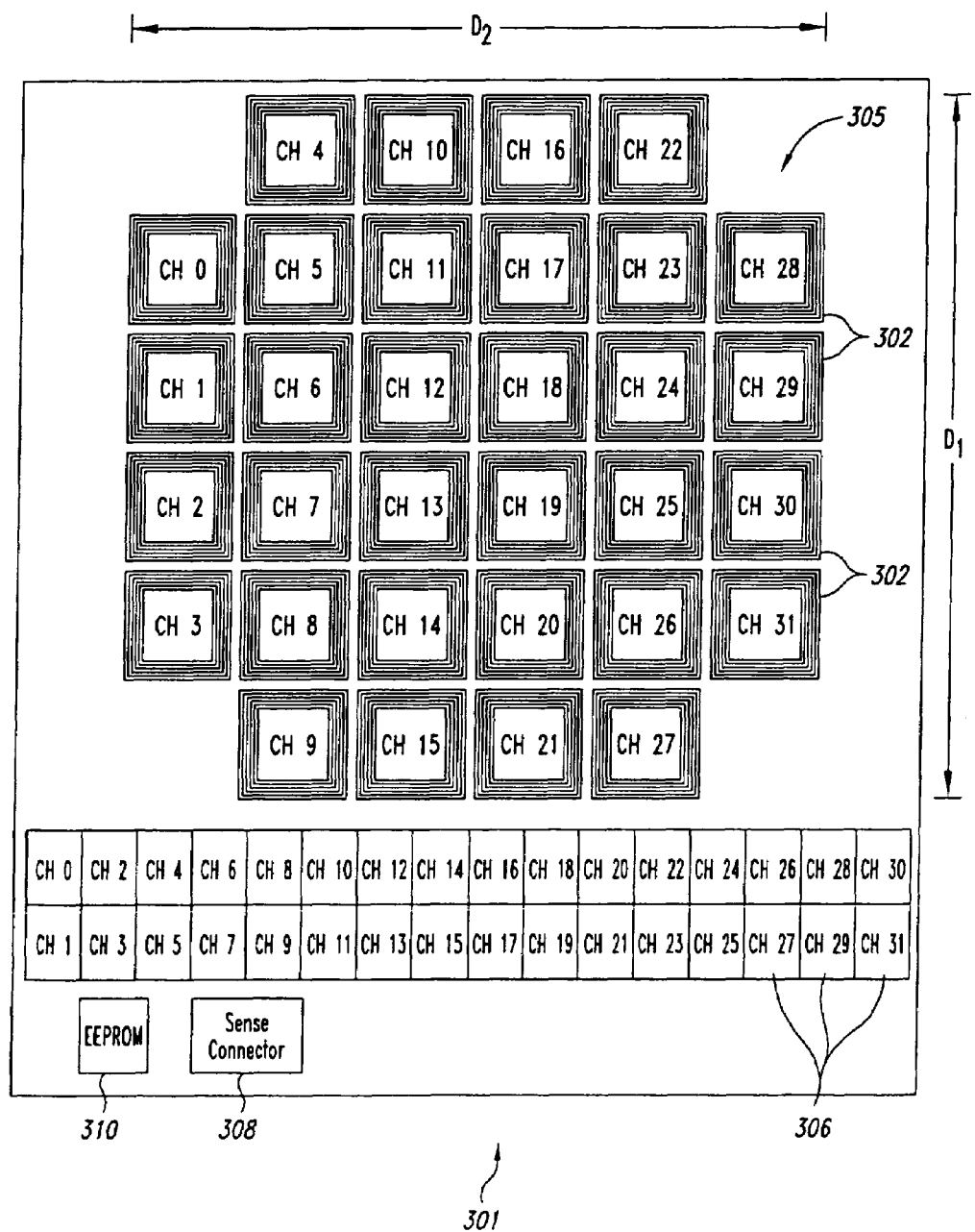
FIG. 3B is a top plan view of an example of a sensing assembly of a sensing subsystem.

FIG. 3B further illustrates an embodiment of the sensing assembly 301. In this embodiment, the sensing assembly 301 includes 32 sense coils 302; each coil 302 is associated with a separate channel 306 (shown individually as channels "Ch 0 through Ch 31"). The overall dimension of the panel 304 can be approximately 40 cm by 54 cm, but the array 305 has a first dimension $D_1$ of approximately 40 cm and a second dimension $D_2$ of approximately 40 cm. The coil array 305 can have other sizes or other configurations (e.g., circular) in alternative embodiments. Additionally, the coil array 305 can have more or fewer coils, such as 8–64 coils; the number of coils may moreover be a power of 2.

The coils 302 may be conductive traces or depositions of copper or another suitably conductive metal formed on the KAPTON® sheet. Each coil 302 has traces with a width of approximately 0.15 mm and a spacing between adjacent turns within each coil of approximately 0.15 mm. The coils 302 can have approximately 15 to 90 turns, and in specific applications each coil has approximately 40 turns. Coils with less than 15 turns may not be sensitive enough for some applications, and coils with more than 90 turns may lead to excessive voltage from the source signal during excitation and excessive settling times resulting from the coil's lower self-resonant frequency. In other applications, however, the coils 302 can have less than 15 turns or more than 90 turns.

As shown in FIG. 3B, the coils 302 are arranged as square spirals, although other configurations may be employed, such as arrays of circles, interlocking hexagons, triangles, etc. Such square spirals utilize a large percentage of the surface area to improve the signal to noise ratio. Square coils also simplify design layout and modeling of the array compared to circular coils; for example, circular coils could waste surface area for linking magnetic flux from the wireless markers 206. The coils 302 have an inner diameter of approximately 40 mm, and an outer diameter of approximately 62 mm, although other dimensions are possible depending upon applications. Sensitivity may be improved with an inner diameter as close to an outer diameter as possible given manufacturing tolerances. In several embodiments, the coils 32 are identical to each other or at least configured substantially similarly.

The pitch of the coils 302 in the coil array 305 is a function of, at least in part, the minimum distance between the marker and the coil array. In one embodiment, the coils are arranged at a pitch of approximately 67 mm. This specific arrangement is particularly suitable when the wireless markers 206 are positioned approximately 7–27 cm from the sensing subsystem 204. If the wireless markers are closer than 7 cm, then the sensing subsystem may include sense coils arranged at a smaller pitch. In general, a smaller pitch is desirable when wireless markers are to be sensed at a relatively short distance from the array of coils. The pitch of the coils 302, for example, is approximately 50%–200% of the minimum distance between the marker and the array.

In general, the size and configuration of the coil array 305 and the coils 302 in the array 305 depend on the frequency range in which they are to operate, the distance from the wireless markers 206 to the array, the signal strength of the markers, and several other factors. Those skilled in the relevant art will readily recognize that other dimensions and configurations may be employed depending, at least in part, on a desired frequency range and distance from the markers to the coils.

The coil array 305 is sized to provide a large aperture to measure the magnetic field emitted by the markers. It can be particularly challenging to accurately measure the signal emitted by an implantable marker that wirelessly transmits a marker signal in response to a wirelessly transmitted energy source because the marker signal is much smaller than the source signal and other magnetic fields in a room (e.g., magnetic fields from CRTs, etc.). The size of the coil array 305 can be selected to preferentially measure the near field of the marker while mitigating interference from far field sources. In one embodiment, the coil array 305 is sized to have a maximum dimension $D_1$ or $D_2$ across the surface of the area occupied by the coils that is approximately 100% to 300% of a predetermined maximum sensing distance that the markers are to be spaced from the plane of the coils. Thus, the size of the coil array 305 is determined by identifying the distance that the marker is to be spaced apart from the array to accurately measure the marker signal, and then arrange the coils so that the maximum dimension of the array is approximately 100%–300% of that distance. The maximum dimension of the coil array 305, for example, can be approximately 200% of the sensing distance at which a marker is to be placed from the array 305. In one specific embodiment, the marker 206 has a sensing distance of 20 cm and the maximum dimension of the array of coils 302 is between 20 cm and 60 cm, and more specifically 40 cm.

A coil array with a maximum dimension as set forth above is particularly useful because it inherently provides a filter that mitigates interference from far field sources. It will be appreciated that in such a configuration the signal strength from the wireless marker decreases proportionally to the square of the distance. However, far field signals from electromagnetic noise generated by other systems in the environment decrease proportionally to the cube of the distance. Thus, if the wireless marker 206 is positioned approximately 20 cm from the sensing subsystem 204, and a diameter or maximum dimension of the sensing subsystem is approximately 40 cm, signals from the wireless marker drop off at a square of the distance from the sensing subsystem while environmental noise drops off at a cube of the distance. The environmental noise is thus filtered by the sensing subassembly 204 to provide better signals to the signal processing subsystem 208.

The size or extent of the array may be limited by several factors. For example, the size of the sensing assembly 301 should not be so large as to mechanically interfere with the movable arm 104 (FIG. 1), the base unit 106 (FIG. 1), or other components, such as a patient couch, rotating gantry of a radiation therapy machine, etc. (not shown in FIG. 1).

Also, the size of the array may be limited by manufacturing considerations, such as a size of available panels 304. Further, making a dimension or width of the coil array 305 larger than twice the distance to the wireless marker 206 may yield little performance improvement, but increase manufacturing costs and increase sensitivity to interference.

The coils 302 are electromagnetic field sensors that receive magnetic flux produced by the wireless marker 206 and in turn produce a current signal representing or proportional to an amount or magnitude of a component of the magnetic field through an inner portion or area of each coil. The field component is also perpendicular to the plane of each coil 302. Importantly, each coil represents a separate channel, and thus each coil outputs signals to one of 32 output ports 306. A preamplifier, described below, may be provided at each output port 306. Placing preamplifiers (or impedance buffers) close to the coils minimizes capacitive loading on the coils, as described herein. Although not shown, the sensing assembly 301 also includes conductive traces or conductive paths routing signals from each coil 302 to its corresponding output port 306 to thereby define a separate channel. The ports in turn are coupled to a connector 308 formed on the panel 304 to which an appropriately configured plug and associated cable may be attached.

The sensing assembly 301 may also include an onboard memory or other circuitry, such as shown by electrically erasable programmable read-only memory (EEPROM) 310. The EEPROM 310 may store manufacturing information such as a serial number, revision number, date of manufacture, and the like. The EEPROM 310 may also store per-channel calibration data, as well as a record of run-time. The run-time will give an indication of the total radiation dose to which the array has been exposed, which can alert the system when a replacement sensing subsystem is required.

While shown in only one plane, additional coils or electromagnetic field sensors may be arranged perpendicular to the panel 304 to help determine a three-dimensional location of the wireless markers 206. Adding coils or sensors in other dimensions could increase total energy received from the wireless markers 206 by 3 dB. However, the complexity of such an array may increase three-fold or more. The inventors have found that three-dimensional coordinates of the wireless markers 206 may be found using the planar array shown in FIG. 3B.

Description of a Suitable Preamplifier

Implementing the sensing subsystem 204 may involve several considerations. First, the coils 302 may not be presented with an ideal open circuit. Instead, they may well be loaded by parasitic capacitance due largely to traces or conductive paths connecting the coils to the preamplifiers, as well as a damping network (described below) and an input impedance of the preamplifiers (although a low input impedance is preferred). These combined loads result in current flow when the coils 302 link with a changing magnetic flux. Any one sense coil 302, then, links magnetic flux not only from the wireless marker 206, but also from all the other sense coils as well. These current flows should be accounted for in downstream signal processing.

A second consideration is the capacitive loading on the coils 302. In general, it is desirable to minimize the capacitive loading on the coils 302. Capacitive loading forms a resonant circuit with the coils themselves, which leads to excessive voltage overshoot when the excitation subsystem 202 is energized. Such a voltage overshoot should be limited or attenuated with a damping or "snubbing" network across the coils 302. A greater capacitive loading requires a lower impedance damping network, which can result in substantial power dissipation and heating in the damping network.

Another consideration is to employ preamplifiers that are low noise. The preamplification can also be radiation tolerant because one application for the sensing subsystem 204 is with radiation therapy systems that use linear accelerators (LINAC). As a result, PNP bipolar transistors and discrete elements may be preferred. Further, a DC coupled circuit may be preferred if good settling times cannot be achieved with an AC circuit or output, particularly if analog to digital converters are unable to handle wide swings in an AC output signal.

Figure 4:
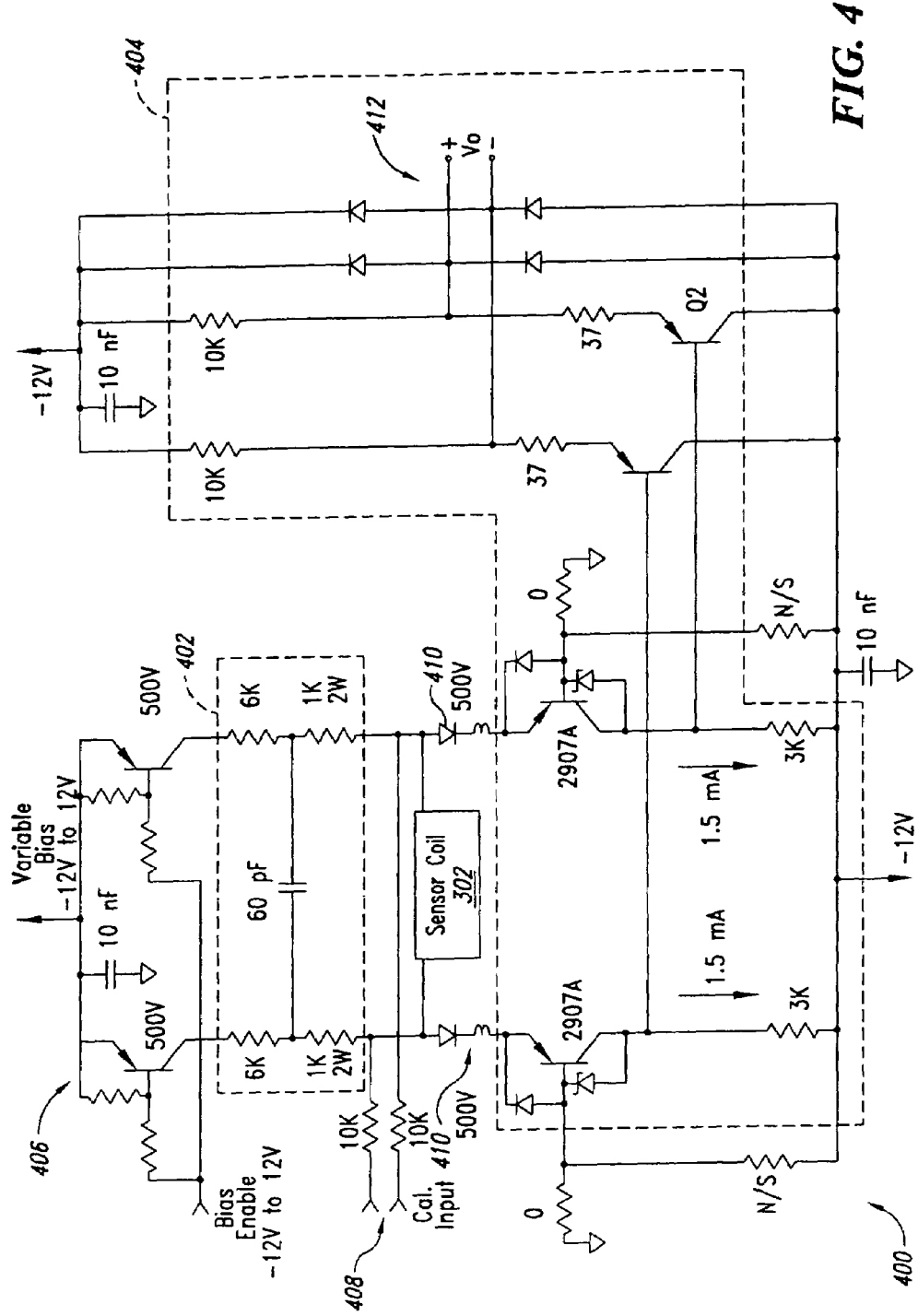
FIG. 4 is a schematic diagram of a suitable preamplifier for use with the sensing subsystem of FIG. 3.

FIG. 4, for example, illustrates an embodiment of a snubbing network 402 having a differential amplifier 404. The snubbing network 402 includes two pairs of series coupled resistors and a capacitor bridging therebetween. A biasing circuit 406 allows for adjustment of the differential amplifier, while a calibration input 408 allows both input legs of the differential amplifier to be balanced. The sensor coil 302 is coupled to an input of the differential amplifier 404, followed by a pair of high voltage protection diodes 410. DC offset may be adjusted by a pair of resistors coupled to bases of the input transistors for the differential amplifier 404 (shown as having a zero value). Additional protection circuitry is provided, such as ESD protection diodes 412 at the output, as well as filtering capacitors (shown as having a 10 nF value).

The Receiver

The signal processing subsystem 208 shown in FIG. 2 is also referred to herein as a receiver. The receiver 208 is operative to receive the signals from the sensing subsystem 204 and perform various signal processing. As set forth below, several of these signal processing techniques and associated structures significantly enhance the performance of the system 100.

Figure 5:
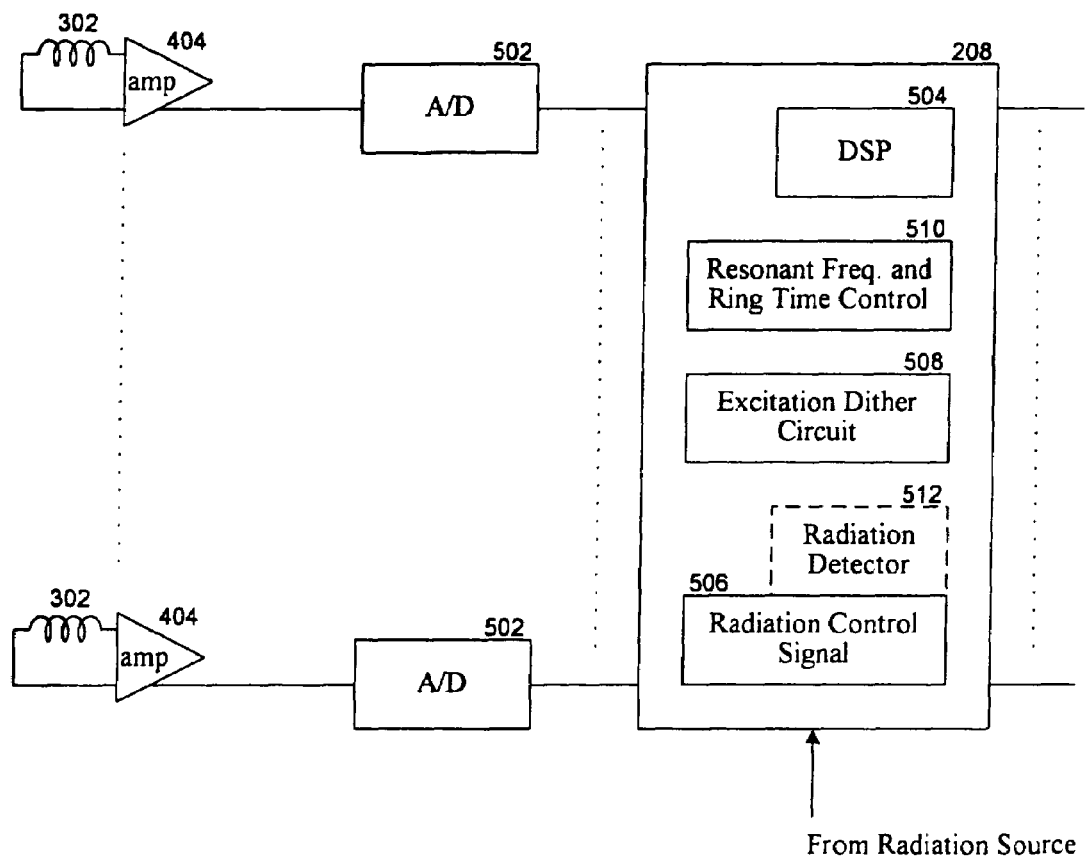
FIG. 5 is a schematic diagram of a receiver formed in accordance with the present invention.

Referring to FIG. 5, the sense coils 32 each provide a signal to a respective amplifier 404. The amplifier then provides the amplified signal to an associated analog-to-digital (A/D) converter 502 that converts the analog amplified signal into a digital representation, such as an 8-bit, 16-bit or 32-bit digital signal, depending upon design considerations. In one embodiment, an out-of band dither is added to linearize the A/D converters 502. Note that the A/D converters 502 are all clocked with a common clock signal to assure uniformity. Further, because the excitation 601 and response 603 waveforms are in the 300–500 KHz range, the A/D 502 would have to sample at a much higher frequency. In one embodiment, the A/D 502 samples at 16 MHz.

Thus, the receiver 208 receives a plurality of digital inputs from the A/D converters 502. As will be seen below, the receiver 208 will act on the plurality of digital inputs to substantially eliminate noise, interference, and other "non-signal" effects to provide a high signal-to-noise ratio (SNR) plurality of digital outputs. These digital outputs can then be used to locate the marker using various locating techniques, such as the ones described in co-pending U.S. patent application Ser. No. 10/679,801 filed Oct. 6, 2003 entitled "Method and System for Marker Localization" and previously incorporated by reference.

Figure 6:
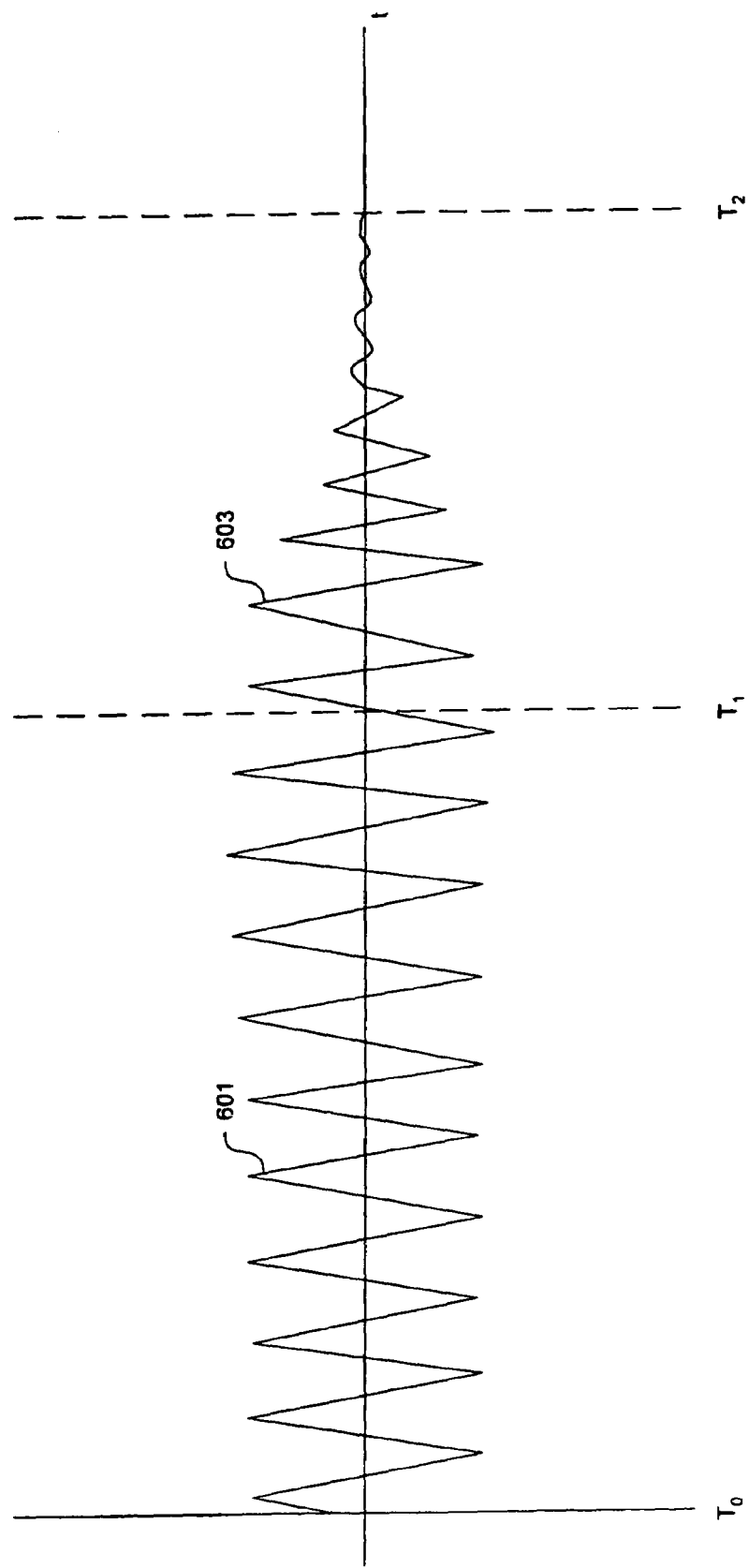
FIG. 6 is a graphical illustration of an excitation pulse and a ringing response signal.

As noted above, the excitation source 202 emits, in one example, a triangular pulse of exciting energy at a frequency of about 300 to 500 kilohertz. FIG. 6 shows one example of such an exciting pulse 601 that is emitted from the excitation source 202. The exciting pulse 601 has a duration of $(T_1-T_0)$. In one embodiment, the duration of the pulse 601 is 16 cycles, or for a signal at 400 KHz, about 40 microseconds. It can be appreciated that shorter or longer excitation pulses 601 may be used depending upon various design parameters.

Note that while a triangular shaped pulse is used for the excitation in one embodiment, other shaped pulses, such as sinusoidal, sawtooth, or square wave excitation may be used. However, a triangular waveform will advantageously excite a marker that exhibits high inductive qualities. Further, because of the relatively high amplitude of the exciting pulse 601, in some circumstances, the coils 302 of the sensing array 204 may be saturated. Further, when the exciting pulse 601 is being emitted, this would ordinarily be a source of significant noise to the coils 302. Because of this, the operation of the system 100 utilizes a time multiplexed methodology where there is an excitation interval ($T_1-T_0$) and a observation interval ($T_2-T_1$).

Thus, after the excitation interval at time $T_1$, the excitation source 202 stops emission and the sensing array 204 "listens" during the observation interval for the decaying ringing response 603 of the marker that has been excited. The ringing response 603 will typically be a damped sinusoidal signal. This observation interval is from time $T_1$ to time $T_2$. In one embodiment, the duration of the listening time is 32 cycles, or for a signal at 400 KHz, about 80 microseconds. The combination of one excitation interval and its following observation interval is referred to herein also as an excitation and observation subinterval.

As will be seen below, in one aspect of the present invention, the excitation interval or observation interval can be adjusted to match the characteristics of the marker. Thus, the length of excitation interval or observation interval is programmable (or automated) in the receiver 208 in order to optimize the sensing system 100. Note that FIG. 6 is not drawn to scale and is merely illustrative.

Because of the relatively short time frames needed to perform the excitation and listening operations (on the order of 120 microseconds), thousands of iterations of the excitation and listening operations can be performed in a single second. In principle, the response signals 603 should be very similar to each other over various cycles of excitation and listening. Thus, in one embodiment, the ringing response signals 603 that are sensed by the coils 302 of the sensing array 204 can be merged over several hundred (or even thousands) excitation and listening cycles to improve the signal-to-noise ratio. In one embodiment, response signals 603 over 100 milliseconds are averaged. This corresponds to roughly 1000 excitation and listening cycles.

Figure 7:
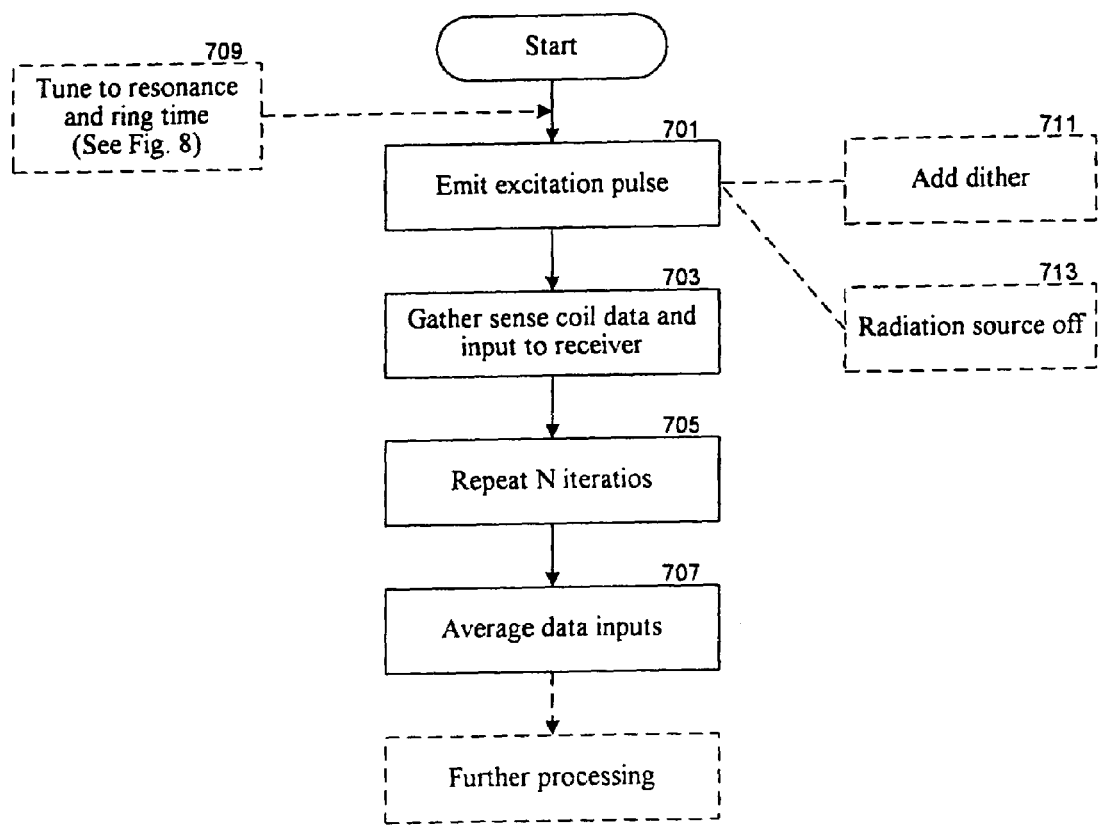
FIG. 7 is a flow diagram illustrating the process of the present invention.

The above process can be seen in FIG. 7 which is a flow diagram of the overall process of one aspect of the present invention. In particular, at box 701, the excitation source 202 emits an exciting pulse 601 during an excitation interval. At box 703, during a observation interval, the sense coils 302 sense the magnetic flux from the marker and provide data as inputs to the receiver 208. This process is repeated for N iterations at box 705 and at box 707, the signals input to the receiver 208 are averaged. Then, further processing is performed on the averaged inputs (see below).

Additionally shown in FIG. 7 are other aspects of the present invention that may be optionally included. These include the implementation of a timing dither at box 711, synchronization to a radiation source to eliminate interference at box 713, and tuning the system 100 to the markers at box 709. All of these aspects are discussed below.

Correlation Receiver

In one embodiment, a correlation receiver is provided. As detailed below, it has been found that coherent receiver design is required to retain the relative polarity of each channel; it will also provide a 3 dB signal-to-noise performance improvement over an incoherent receiver.

The response signals 603 that are received by the coils 302 and input into the receiver have an unknown phase. Thus, the plurality of inputs are complex signals that each have an in-phase component and a quadrature component. The coherent receiver 208 operates by extracting these components of the inputs.

The phase shift occurs because the marker oftentimes does not have a resonant frequency that is precisely matched to the exciting pulse 601. This is due to manufacturing tolerances and other factors. Because of the mismatch between the resonant frequency of the marker and the exciting pulse 601, there will be a phase component of the signal sensed by the coils 302. Further, in the presence of a strong magnetic signal, the markers may enter saturation in which case there is a phase shift due to losses in the marker.

However, it has been found that the phase shift is substantially the same for all channels (i.e. each coil). As will be seen below, the receiver analyzes the signals from all of the channels and determines the most likely phase shift. Once the phase shift has been determined, this phase shift is corrected from the signals (such as by removal) and the real portion of the signal can be extracted. By performing the estimation and removal of the phase shift, this is substantially equivalent to coherent detection of the input signals. In one embodiment, the coherent detection is implemented by a digital signal processor 504. However, in alternative embodiments, the processing or analysis can be done using programmable logic devices or even software running on a general purpose microprocessor.

Receiver Tunable to Resonator Frequency and Ring Time

As noted above at box 709 of FIG. 7, in another aspect of the present invention, the receiver 208 is adaptable to work in coordination with the excitation source to tune the system 100 to the specific characteristics of the marker. Specifically, the excitation source 202 has an adjustable frequency that can be tuned in accordance with analysis made by the receiver 208.

Because of various manufacturing variances and other factors, the marker may not have an accurately predictable resonant frequency. Thus, the receiver 208 identifies the resonant frequency of the marker and provides that information to the excitation source 202. The excitation source 202 can then provide an exciting pulse 601 at a frequency that is closely matched to the resonant frequency of the marker. In this manner, better performance can be obtained by the system 100.

In one embodiment, the determination of the resonant frequency of the marker is done in an iterative manner. The process of detailed in FIG. 8, where at box 801, the excitation source 202 emits an exciting pulse 601 at a starting frequency $F_s$. In one embodiment, the starting frequency is the lower range of possible resonant frequencies for the marker. Depending upon manufacturing tolerances, the marker may have a wide marker resonant frequency range, for example, between 300–500 KHz. In this example, $F_s$ would then be 300 KHz.

Next, at box 803, data from the sense coils 302 is gathered by the receiver 208 and stored. At box 805, the frequency of the last emitted exciting pulse 601 is incremented by an amount $\Delta F$. The value of $\Delta F$ is variable and depends upon the amount of resonant frequency accuracy desired for the system 100. However, in one embodiment, $\Delta F$ is 2 KHz. The process is repeated until an ending frequency $F_e$ has been reached, for example 500 KHz. The frequencies of the exciting pulses ranging from $F_s$ to $F_e$ incremented by $\Delta F$ constitute a set of frequencies used to excite the marker. This set of frequencies may be large or small depending upon the $\Delta F$, $F_s$ and $F_e$.

In alternative embodiment, the spacing $\Delta F$ is chosen as a fixed percentage bandwidth which has advantages in accuracy and/or processing time in certain applications particularly when the marker Q (rather than bandwidth) tends to be constant over a large frequency range. One such approach would use a step size approximating the half power points of the marker frequency response. An example would be 1.5% steps resulting in a set consisting of: 300.00, 304.50, 309.07, . . . , 497.70, 505.16 kHz. It is understood that depending on the marker characteristics, other sets of excitation frequency may be used and the invention accepts an arbitrary arrangement of excitation frequencies.

Next, at box 809, the data received for these iterations is analyzed and the frequency for the emitting pulse 601 that provided the strongest (or otherwise best) signal is chosen as the resonant frequency of the marker at box 811. The data may also be referred to as a resonance set of plurality of inputs from the sense coils 302. It can be appreciated that various methods for determining the resonant frequency may be possible and that only one implementation is given herein. The process above may be implemented, for example, in a resonant frequency and ring time control processor 510.

An alternative method of determining the resonant frequency would interpolate the resultant response. This is particularly beneficial if the set of frequencies can guarantee multiple samples within a marker frequency response bandwidth. It is understood that this interpolation can be conducted in a number of ways, two examples of which are: a) parabolic fitting to find an estimate of the peak signal value and resonant frequency using neighboring data points to the one that represents the highest energy response; or, b) least squares error fitting to a multi-parameter model of the marker frequency response.

Figure 8:
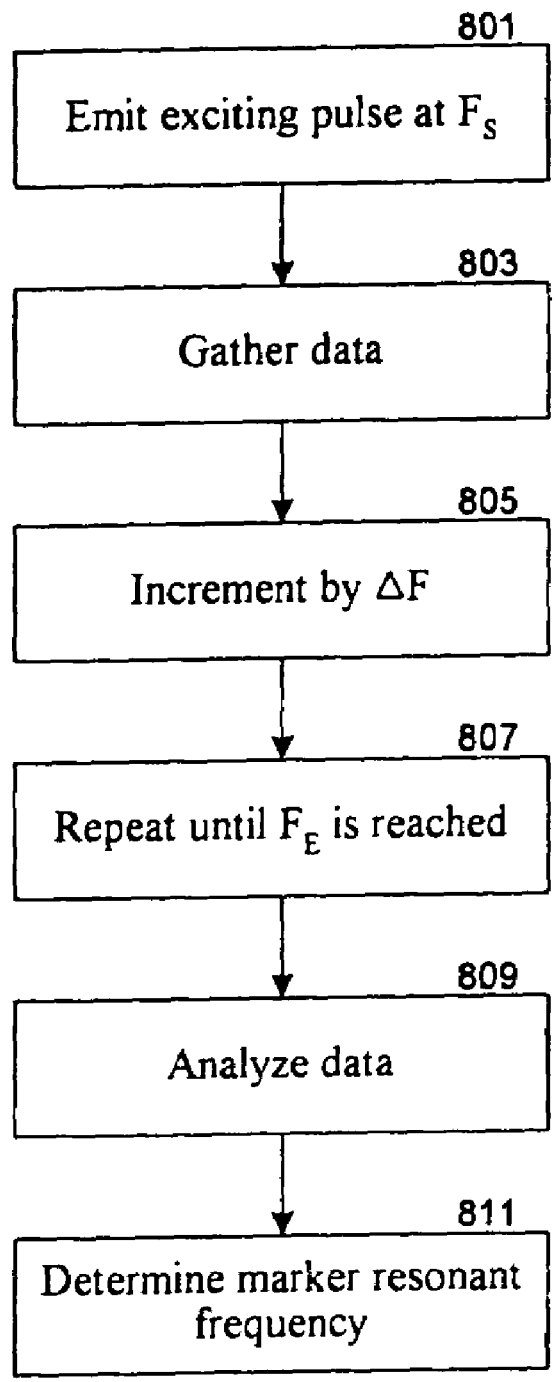
FIG. 8 is a flow diagram illustrating the process of determining a resonant frequency of a marker.

In yet another alternative embodiment to the process of FIG. 8, the frequency range may be searched with a sparse set of excitation frequencies. Then, the excitation is iterated with a higher resolution set of frequencies in the neighborhood surrounding the candidate resonant frequency. Multiple iterations may be used in combination with interpolation.

In other words, a first set of frequencies that are relatively sparsely spaced is used to excite the marker. Based upon the information received by the receiver 208, the marker resonant frequency can be narrowed down. A second set of frequencies that is more densely populated around the frequency band of interest (as ascertained by the first set of frequencies) is then used to excite the marker. This process can be repeated until the desired resolution of the marker resonant frequency has been obtained.

Yet another embodiment of the process of FIG. 8 would use wide-bandwidth excitation signals rather than sinusoidal signals that could excite multiple markers at once and then process the data, for example, using spectral estimation techniques, to determine the resonant frequencies of the markers. An example of such a signal would be a high energy pulse, shaped to concentrate its energy in the frequency band of interest. In addition, the signal could be repeated multiple times and averaging employed to improve the sensitivity of the resonant frequency estimation.

Subsequent excitation is performed at the marker resonant frequency. Further, the receiver 208 is adjusted to correlate using the marker resonant frequency. This type of initial "calibration" by identifying the appropriate excitation frequency has been found to provide advantageous results.

Additionally, the receiver 208 may be is adapted to the ring time of the marker. Various marker designs may have varying ring times. For example, some markers made from certain materials may have ring times that extinguish quite rapidly compared to other markers made of differing material. Because of this, it may be advantageous to adjust the excitation pulse interval and the observation interval.

In the example given above, an excitation pulse of 16 cycles and a listening time of 32 cycles is used. However, these parameters may need to be changed depending upon operating conditions and marker variations. Therefore, in accordance with the present invention, the receiver 208 has control circuitry that can control the operation of the excitation source 202 not only in the frequency domain, but also the time domain for the exciting pulse 601. The receiver 208 includes the resonant frequency and ring time control processor 510 that can modify the length of the observation interval. These parameters may be controlled according to preprogrammed instructions or manually by the operator of the system 100 through a user interface.

In accordance with another aspect of the present invention, the receiver 208 also includes signal processing that uses a weighting of the data obtained during the observation interval. This is also referred to as applying a "window" filter to the observation interval. In one embodiment, the window is a Blackman window. The effect of the Blackman windowing is to improve the frequency selectivity of the receiver by reducing the effects of other markers tuned to different frequencies.

In another embodiment the window filter is a "matched filter" that has a window that emulates the decay signature of the marker resonance. The effect of the matched filter windowing is to improve the sensitivity of the receiver.

In some applications, more than one marker is within the field of interest. Typically, three different markers having varying resonant frequencies are used. Because of this, all three markers may have a response to the exciting pulse 601 at the resonant frequency of one of the markers. The signals from the two other markers may add noise to the desired signal to be detected by the receiver. Because of this, as will be seen below, various windows can be applied to reduce the sensitivity of the receiver to other markers in the field of interest. Still, one drawback of the window filtering is decreased sensitivity to the marker of interest.

The spectral data can be simultaneously used to improve detection robustness of real markers versus noise spikes. In one embodiment of the system, the data is checked for consistency with the marker frequency response model. The system can reject candidates if the estimated bandwidth does not conform to the design parameters of the markers, for example, having a bandwidth outside of the acceptable manufacturing tolerance range. Additional model characteristics that may be distinguished include acceptable energy levels and acceptable separations of markers in the frequency domain. The system can also reject signals that are not coherent with the excitation signal phase as characterized by independent sources of noise in the environment.

Synchronization with Radiation Beam

In one application of the present invention, the system 100 is used in proximity to a radiation source (such as a linear accelerator or a particle beam accelerator) that is used for the treatment of a human, such as during radiation therapy of a cancer patient. In such an instance, the system 100, and particularly, the receiver 208, the markers, or the sensing coils may be adversely interfered with by the operation of radiation source (not only the emitted radiation, but the circuitry of the radiation source itself). Therefore, the system 100 is adapted to operate when the radiation source is off. This can be coordinated, for example, by the use of a radiation control signal 506 (see FIG. 5) between the radiation source and the receiver 208 and/or system 100. When the radiation source is active, the control signal travels to the receiver 208 and/or system 100 in order to put the system 100 into a "standby" mode. The radiation control signal may be a simple binary signal.

As one example, radiation may be delivered by the radiation source in a 150 microsecond burst, occurring once every 10 milliseconds. In the example given previously, one excitation and listening cycle may take approximately 120 microseconds. Therefore, in one embodiment, after a radiation burst (when the system 100 is in standby mode), perhaps on the order of 80 excitation and listening cycles may be performed by the system 100 until the next radiation burst. This aspect of the present invention helps to negate the effect of any interference from the radiation source.

It is perhaps easiest to implement a control signal line between the radiation source and the system 100 to indicate when the radiation burst is occurring. However, this may not be commercially possible since the manufacturers of the radiation equipment and the vendors of the marker location equipment may not be able to coordinate these interface issues.

Therefore, in an alternative embodiment, the receiver 208 includes a matched filter or other device (designated as radiation detector 512) that can detect the presence of interference due to the operation of the radiation delivery apparatus, or any other interfering device that operates in a pulsed mode. If such interference is detected, then the receiver 208 is operative to discard received input signals from the coils 302 that occurred in that timeframe.

Receiver and Exciting Source Configured for Pseudo-Random Excitation

The primary function of the receiver 208 is to suppress noise and interference, while extracting signal from the received inputs. As noted above, one of the techniques used for suppressing noise is to perform averaging over several observation intervals. However, it has been found that if the source of noise is periodic with a periodicity matched to that of the excitation and observation interval, then the noise not only will not be removed by averaging, but may indeed masquerade as signal.

Several sources of noise and interference that may have the periodicity include computer equipment, cathode ray tube monitors, medical equipment, and other electronics. In order to suppress this type of periodic noise, in another aspect of the present invention, the initiation of each excitation pulse 601 is changed so as to not have a periodic repetition.

In accordance with the present invention, the receiver 208 includes a pseudo-random excitation dithering circuit 508 (see FIG. 5) that will randomly offset the start timing of each exciting pulse 601 relative to previous or future exciting pulses. In one embodiment, the dithering circuit 508 will offset the timing of each exciting pulse 601 by a random fraction of one period of the carrier frequency of the exciting pulse 601, e.g., at 400 KHz dither from 0 to 2.5 microseconds. The effect of the dithering would spread out or "decohere" any periodic noise, turning the periodic noise into random noise that can be reduced by signal processing.

Another method of achieving a similar result is the randomly vary the polarity of each exciting pulse 601. For example a first exciting pulse may start with a positive going cycle, while a second exciting pulse may start with a negative going cycle. In other words, the first exciting pulse may be 180 degrees out of phase with the second exciting pulse. This random polarity of the exciting pulses 601 will also decohere any periodic noise, turning the periodic noise into random noise that can be eliminated by signal processing.

Yet another method of achieving a similar result is the randomly vary the starting phase of each exciting pulse 601. For example a first exciting pulse may start with zero relative phase, while a second exciting pulse may start at some random phase, while a third exciting pulse may start at another random phase. This random starting phase of the exciting pulses 601 will also decohere any periodic noise, turning the periodic noise into random noise that can be eliminated by signal processing.

Frequency Orthogonality

In the foregoing embodiments described, the excitation intervals and observation intervals are orthogonal temporally. In other words, the excitation intervals are distinct from the observation intervals and there is no overlap. In another embodiment, the receiver 208 may be used with a substantially continuous excitation pulse. In order to avoid interference, the excitation pulse is at a first frequency that is different from the returned frequency of the marker. This is referred to as frequency orthogonality. Because of this, the receiver 208 is adapted to have a narrow bandpass filter to suppress the excitation frequency and pass the returned frequency.

Mathematical and Signal Processing Foundation

As noted above, the receiver 208 uses coherent detection to increase SNR. Assume that the marker signal sensed by each channel is applied to a complex correlation receiver, identical over all channels. It is further assumed that any unknown phase shift in the marker signal is, in the absence of noise, common across all channels. If the actual phase—referred to as $\phi$—were known, coherent reception could be effected by counter-rotating each estimate by this phase and discarding the imaginary parts. This is a linear operation, and the only discarded component is the part of the noise that is orthogonal to the signal.

Any estimate of $\phi$ from the data will be inexact. In a single channel case, an estimate of $\phi$ will be corrupted by noise. However, the presence of multiple channels (i.e. multiple sense coils 302) permits a better estimate of the necessary phase.

Quasi-Coherent Detection Using Least-Mean Squares Estimate of the Signals

Figure 9:
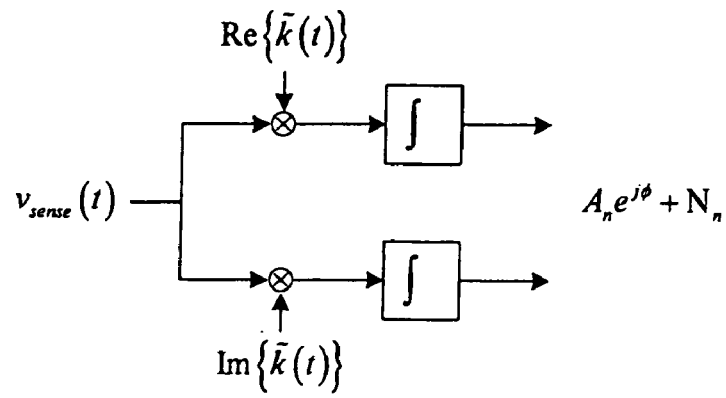
FIG. 9 is a block diagram of a portion of the processing of one channel of the receiver.

Consider multiple identical receiver channels in which the outputs of the integrators are sampled at the end of a common measurement interval, as in FIG. 9 depicting the $n^{th}$ channel.

The output of each channel at the end of each measurement interval can be modeled as in FIG. 9, where $A_n$ is the signed scalar amplitude of the desired signal, $\phi$ is an unknown phase shift common to all channels, and $N_n$ is a complex zero-mean, uncorrelated error in the measurement. The data can be fit to the model in a least mean squares (LMS) sense as follows.

Let the data of the $n^{th}$ channel be represented as $x_n + jY_n$. The sum of the square magnitudes of the errors between the model and the data is thus $$E = \sum_n |A_n e^{j\phi} - (x_n + jy_n)|^2$$
$$= \sum_n A_n^2 + (x_n^2 + y_n^2) - 2A_n[x_n\cos\phi + y_n\sin\phi]$$

where the summation is taken over all channels. The model parameters $A_n$ and $\phi$ are chosen to minimize this quantity. Denoting the total number of channels as $N_{ch}$, the problem is one of determining $N_{ch}+1$ parameters from $2\,N_{ch}$ data points.

The partials of the equation above with respect to the parameters are $$\frac{\partial E}{\partial A_n} = 2A_n - 2[x_n\cos\phi + y_n\sin\phi]$$

$$\frac{\partial^2 E}{\partial A_n^2} = 2$$

$$\frac{\partial E}{\partial \phi} = \sum_n 2A_n[x_n\sin\phi - y_n\cos\phi]$$

$$\frac{\partial^2 E}{\partial \phi^2} = \sum_n 2A_n[x_n\cos\phi + y_n\sin\phi]$$

A solution that makes the first partials vanish, and keeps the second partials positive, is $$\boxed{\begin{aligned}\hat{A}_n &= x_n\cos\hat\phi + y_n\sin\hat\phi \\ \hat\phi &= \frac{1}{2}\text{Arg}\left\{\sum_n (x_n + jy_n)^2\right\}\end{aligned}} \quad \text{Eq. 1}$$

Note that the hat notation is used to distinguish the estimates of the parameters from the actual values. The expression for $\hat{A}_n$ is simply the rule for counter-rotating each measurement through $\hat\phi$ and taking the real part. The expression for $\hat\phi$ is intuitively satisfying; it specifies that each complex data point should be squared (hence doubling its phase), and summed with all others. The phase of the result is twice the phase of the estimate of $\phi$. Note, though, that halving the calculated phase yields two solutions, separated by $\pm\pi$.

This results in a sign ambiguity in the estimate of $A_n$. This ambiguity is benign, as it applies to all channels in common for the measurement interval used. If post-detection averaging (or an equivalent operation) is intended, then this ambiguity will have to be resolved. When the SNR is high, this is easy to do by looking at the data.

Noise Performance of Quasi-Coherent Detection

It can be shown that, when the phase estimate is expressed in terms of its error $$\hat\phi = \phi + \psi$$

then the estimate of the signal in the $k^{th}$ channel is $$\hat{A}_k = A_k\cos\psi + \varepsilon_k\cos\psi + \delta_k\sin\psi \quad \text{Eq. 2}$$

where $$2\psi = \text{Arg}\left\{\left[\sum_n A_n^2 + 2A_n\varepsilon_n + (\varepsilon_n^2 - \delta_n^2)\right] + j\left[\sum_n 2A_n\delta_n + 2\varepsilon_n\delta_n\right]\right\}$$

To keep the notation as simple as possible, the ambiguity in the sign of the estimate is suppressed in the following development, although it should keep in mind.

The noise components $\varepsilon_k$ and $\delta_k$ are modeled as circular Gaussian random variables, with identical variances $\langle e^2\rangle = E\{\varepsilon_k^2\} = E\{\delta_k^2\} = E\{|N|^2\}/2$.

To examine the performance of this detector in the presence of noise, the expected value and the second moment of Eq. 2 can be calculated.

$$E\{\hat{A}_k\} = A_k E\{\cos\psi\} + E\{\varepsilon_k\cos\psi\} + E\{\delta_k\sin\psi\}$$

$$E\{\hat{A}_k^2\} = \frac{A_k^2}{2} + \frac{A_k^2}{2}E\{\cos2\psi\} + \frac{1}{2}E\{\varepsilon_k^2 + \delta_k^2\} + \frac{1}{2}E\{(\varepsilon_k^2 - \delta_k^2)\cos2\psi\} + A_k E\{\varepsilon_k\cos2\psi\} + A_k E\{\delta_k\sin2\psi\} + E\{\varepsilon_k\delta_k\sin2\psi\}$$

Because $\psi$ is a function of the noise components, the expectations are not straightforward to calculate. It is shown below that, under conditions of high SNR, we may approximate $$E\{\hat{A}_k\} \cong A_k + \frac{A_k\langle e^2\rangle}{2\sum_n A_n^2} \quad \text{Eq. 3}$$

$$E\{\hat{A}_k^2\} \cong A_k^2 + \frac{A_k^2\langle e^2\rangle}{\sum_n A_n^2} + \langle e^2\rangle$$

The signal-to-noise ratio of the $k^{th}$ receiver channel, assuming ideal coherent detection, is $A_k^2/E\{\varepsilon_k^2\}$; the signal-to-noise across all channels is thus $$SNR = \frac{\sum_n A_k^2}{N_{ch}\langle e^2\rangle}$$

In terms of the SNR, the moments calculated above are $$E\{\hat{A}_k\} \cong A_k\left[1 + \frac{1}{2N_{ch}SNR}\right]$$

$$E\{\hat{A}_k^2\} \cong A_k^2\left[1 + \frac{1}{N_{ch}SNR}\right] + \langle e^2\rangle$$

When the SNR and the channel count are sufficiently large that the bracketed terms can be neglected, these moments approach the coherent case. Note that it is necessary for both the SNR and the channel count to be large compared to unity; when $N_{ch}=1$, quasi-coherent detection devolves to incoherent detection.

While Eq. 3 exhibits a bias in the estimate of $A_k$, this bias should be small in a system where the SNR is expected to be in excess of 40 dB and the number of channels around 32.

Coherent Detection using Disjoint Measurement Intervals

In the above, it is assumed that the available data was limited to one measurement interval, each measurement interval consisting of a large number of excitation intervals and observation intervals (sub-intervals). In practice, the system 100 will make measurements continually, and there will be a series of past measurements to exploit.

Referring to Eq. 1, disjoint measurement intervals are used for the estimates of $A_n$ and $\phi$. Let the data from the prior measurement interval be used to calculate $\hat{\phi}$, and let the data from the current measurement interval be used to calculate $\hat{A}_n$. This decorrelates the noise of the current measurement from the error in the estimate $\hat{A}_n$, and the resulting statistics are different in the following way.

Because the noise components $\epsilon_k$ and $\delta_k$ are statistically independent from $\cos\psi$ and $\sin\psi$, the equations above can be simplified to $$E\{\hat{A}_k\} = A_k E\{\cos\psi\}$$

$$E\{\hat{A}_k^2\} = \frac{A_k^2}{2} + \frac{A_k^2}{2}E\{\cos 2\psi\} + \frac{1}{2}E\{\epsilon_k^2 + \delta_k^2\}$$

Eq. 4

These can be approximated $$E\{\hat{A}_k\} \cong A_k - \frac{A_k \langle e^2 \rangle}{2\sum_n A_n^2}$$

$$E\{\hat{A}_k^2\} \cong A_k^2 - \frac{A_k^2 \langle e^2 \rangle}{\sum_n A_n^2} + \langle e^2 \rangle$$

At first blush, this appears to differ from Eq. 3 only superficially. However, the decorrelation of the errors means that this technique can be modeled exactly as a coherent receiver with a small phase error in the correlation kernel. The small phase error results in a scale factor error, with expectation $$\left[1 - \langle e^2 \rangle \Big/ \left(2\sum_n A_n^2\right)\right];$$

that is constant across all channels, so the results remain ratiometrically accurate.

This technique relies on the stationarity of the phase shift between measurement intervals. However, performance is robust; for example, a phase error of 27° results in only a 1 dB scale factor error.

The Linear System Model

The relationship between a signal output by a marker 206 in response to an excitation from the excitation system 202 is modeled as follows. Assuming that marker saturation effects are neglected, a "marker transfer response" can be modeled as a second order bandpass function:

$$H_b(s) = \left[\frac{RCs}{L_b C s^2 + RCs + 1}\right]$$

with corresponding impulse response $h_b(t)$.

Figure 10:
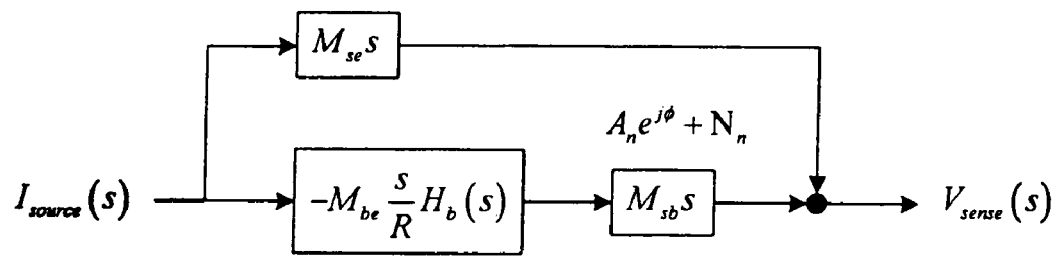
FIG. 10 is a block diagram in the frequency domain of a model for the coupling between the excitation pulse and the response signal.

The coupling between the current in the excitation source 202 and the voltage sensed by a sensing coil 302 can be represented as a linear system shown in FIG. 10. As seen, an upper path through box 1001 is a direct feedthrough from source to sensor. A bottom path is the response of the marker as seen by the sensing coil 302. The transfer function is thus:

$$\frac{V_{sense}(s)}{I_{excitation}(s)} = M_{se}s - \frac{M_{be}M_{sb}}{R}s^2\left[\frac{RCs}{L_b C s^2 + RCs + 1}\right]$$

Figure 11:
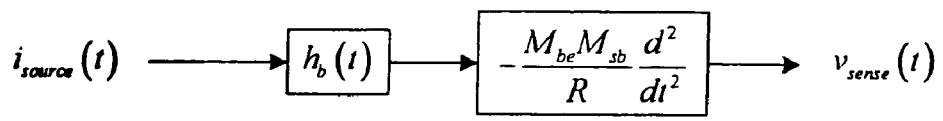
FIG. 11 is a block diagram in the time domain of a model for the coupling between the excitation pulse and the response signal where the direct path is ignored.

If the direct feedthrough path is ignored, a time domain block diagram of the linear system model is given by FIG. 11, where the filtering function is performed by convolution.

Analytic Signal Model

Assuming that bandpass signals are being processed, let:

$$\tilde{p}(t) = -j\frac{A_e}{2}e^{j\omega_e t}\mathrm{rect}(t/\tau_e)$$

$$= -j\sqrt{\frac{E_e}{2\tau_e}}e^{j\omega_e t}\mathrm{rect}(t/\tau_e)$$

be the analytic representation of the excitation pulse p(t) (i.e., the current in the excitation source coil).

Hence $$p(t) = 2\,\mathrm{Re}\{\tilde{p}(t)\}$$
$$= A_e \sin(\omega_e t)\mathrm{rect}(t/\tau_e)$$

$$\int dt\, p^2(t) = 2\int dt|\tilde{p}(t)|^2$$
$$= E_e$$

Here, $A_e$ is the amplitude of the pulse, $\tau_e$ is its duration, and $E_e$ is its energy. They are related according to $E_e = A_e^2 \tau_e/2$. Note that $\tilde{p}(t)$ is not strictly analytic, except in the limit of arbitrarily long pulse duration. As a consequence, the integrals for the energy are not strictly equal unless $\tau_e$ is an integral number of periods; we assume this is always the case and does not materially affect the conclusions herein.

We also approximate the analytic representation of the impulse response of the resonant marker as $$\tilde{h}_b(t) = \sigma_b e^{s_b t}\mu(t)$$

This is a single pole response that is accurate for a broad range of frequencies around the marker's resonant frequency, provided that Q is sufficiently high, where $$\zeta = \frac{1}{2Q} \quad \text{damping factor}$$

$-\sigma_b = -2\pi\zeta f_b$, real part of the pole $\omega_b = 2\pi\sqrt{1-\zeta^2} f_b$, imaginary part of the pole $s_b = -\sigma_b + j\omega_b$, beacon's natural frequency $\mu(t) = [1+\mathrm{sgn}(t)]/2$ unit step function A Closed Form Expression for the Sensed Voltage from a Single Pulse Using the analytic representations for the pulse and the marker impulse response, the analytic representation of the sensed voltage in FIG. 11 can be obtained. To examine the effects of multiple markers and marker/source mismatch, it is assumed that the excitation frequency is different from the marker's resonant frequency ($\omega_b$), i.e., $\omega_e$ is distinct from $\omega_b$. It is helpful to define another natural frequency that arises from the excitation.

$$s_\Delta = -\sigma_b + j\omega_b - j\omega_e$$

The receiver thus "sees" the following signal from the marker as [Eq. 4]:

$$\tilde{v}_{sense}(t) = -\left[\frac{M_{be}M_{sb}}{R}\right]\frac{d^2}{dt^2}\{\tilde{p}(t) * \tilde{h}_b(t)\}$$

$$= -\left[\frac{M_{be}M_{sb}}{R}\right]\frac{d^2}{dt^2}\left\{\int_0^\infty dx\,\tilde{p}(t-x)\tilde{h}_b(x)\right\}$$

$$= -j\left[\frac{M_{be}M_{sb}}{R}\right]\frac{A_e}{2}\frac{s_b^2\sigma_b}{s_\Delta}e^{s_b t}\begin{cases}0; & t < -\tau_e/2 \\ \left[1-\frac{s_\Delta}{s_b}\right]^2 e^{-s_\Delta t} - e^{s_\Delta \tau_e/2}; & -\tau_e/2 \leq t \leq \tau_e/2 \\ e^{-s_\Delta \tau_e/2} - e^{s_\Delta \tau_e/2}; & \tau_e/2 < t\end{cases}$$

There are three temporal regimes: prior to excitation, during excitation, and after excitation. In the third regime, the received signal reverts to the marker natural frequency, weighted with a complex term that is a function of the difference frequency between excitation and resonance.

Figure 12:
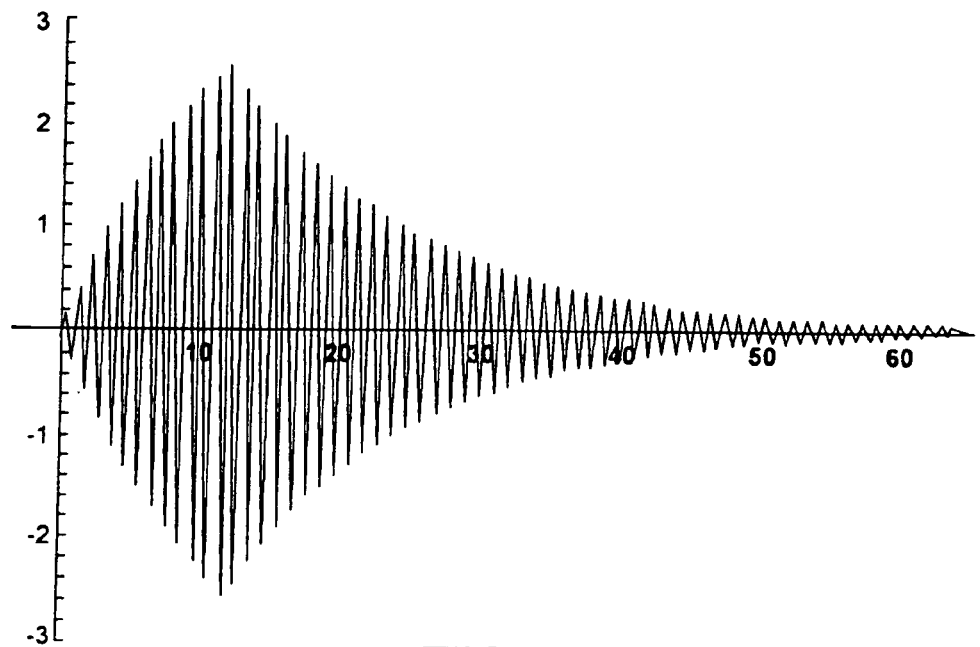
FIG. 12 is an example of a response signal from a marker when the excitation pulse is at resonance to the marker resonance.

FIG. 12 illustrates one example of a sensed response from a marker when it is excited at resonance with a 12-cycle, 100 kHz pulse. It is the real part of Eq. 4 with Q=40 and $f_b=10^5$.

Figure 13:
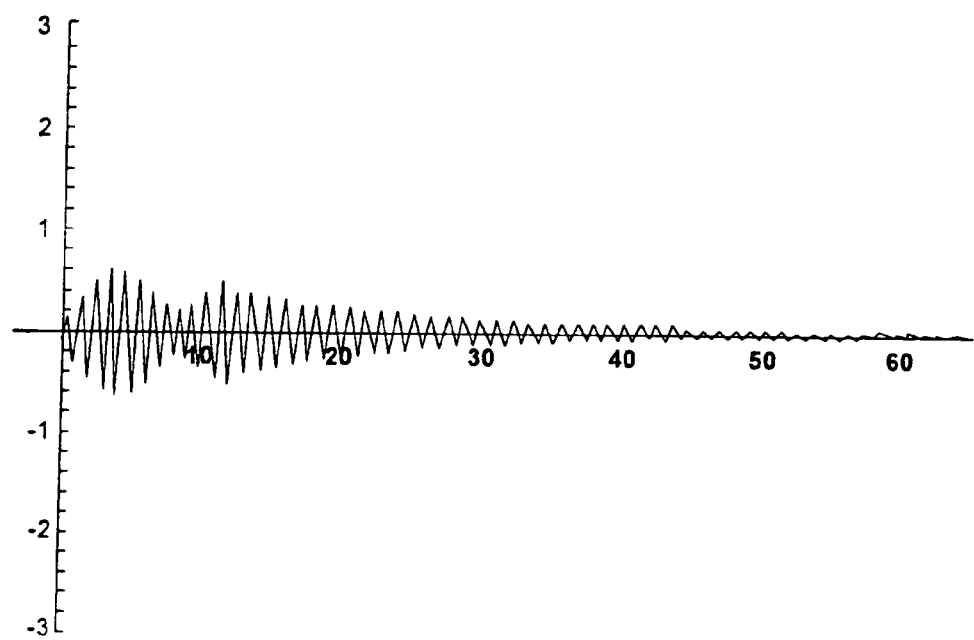
FIG. 13 is an example of a response signal from a marker when the excitation pulse is off resonance to the marker resonance.

FIG. 13 shows the sensed response of a marker excited off-resonance. The same excitation pulse is used, but the marker is tuned to 88 kHz. The difference frequency is clearly visible, as is the marker's natural frequency decay. It is also clear that the excitation selectivity is poor, as the response of the 88 kHz marker is suppressed only by a factor of about five.

Marker Saturation and Coherent Detection

Marker saturation is problematic, presenting both analytic and practical difficulties. Qualitatively, the effects of marker saturation on the sensed voltage will be as follows.

The peak of FIG. 12 will flatten out to a value relatively independent of the excitation amplitude.

During the excitation interval, the effective resonant frequency of the marker will increase, and the effective Q will decrease.

At the beginning of the observation interval (the third regime of Eq. 4), the marker will relax out of saturation and decay in a linear fashion according to its natural frequency. However, we have to expect that its initial conditions in this interval are, in practice, unknowable. In particular, the phase of the response in the observation interval has to be treated as a random variable.

Give the above, it has been found that the signal in the observation interval is relatively independent of the coupling term $M_{be}$, the derivative operator associated with the induction between the source and marker, and the duration of the excitation interval. Accordingly, a model for the analytic sensed voltage in the observation interval can be simplified to:

$$\tilde{v}_{sense}(t) = \left[\frac{M_{sb}}{R}\right]\frac{A_{sat}}{2}s_b e^{s_b(t-\tau_e/2)}; \tau_e/2 < t$$

where $A_{sat}$ is a complex random variable.

The proper selection of $\tau_e$ (the duration of the excitation interval), $\tilde{k}(t)$ (the complex correlation kernel), and the repetition interval of the excitation pulses is important for optimum performance. The selection may be made on an empirical basis and experimental data may be used to determine these parameters.

Relative Sensitivity of a Coherent Detector: Single Pulse

There are sensitivity/selectivity trade-offs in the context of sub-optimal correlation kernels. An optimum correlation kernel refers to a kernel which maximizes the SNR in a white noise environment. In an environment with multiple markers at different frequencies, there are better choices for kernels. The response of a receiver to a marker as the system frequency changes is examined, i.e. predicting receiver sensitivity as a function of frequency. Herein, the total measurement interval is denoted as $T_0$.

There are three different cases examined:

Case 1: The linear system model applies. The receiver sensitivity over frequency is referenced to a case in which the marker is excited with a constant energy CW signal, at its resonant frequency, where the energy in the pulse is equal to the energy in the CW excitation. In this case, at marker resonance, the relative sensitivity equals the efficiency. The use of a constant energy comparison is meaningful when the energy in the pulse is limited by, for example, thermal or average exposure considerations.

Case 2: The linear system model applies. The receiver sensitivity over frequency is referenced to a case in which the marker is excited with a constant amplitude CW signal, at its resonant frequency, where the amplitude in the pulse is equal to the amplitude of the CW excitation. The use of a constant amplitude comparison is meaningful when the energy in the pulse is limited by, for example, source current or peak exposure considerations.

Case 3: All markers in the field are saturated. This is generally not realistic when markers of different resonant frequencies are present, but the conclusions drawn are nonetheless instructive.

Case 1: Constant Energy

The CW Reference

The reference in this case assumes CW excitation exhibiting constant energy $E_0$ over the measurement interval (same as the observation interval), independent of its duration, at the marker's resonant frequency. The sensed voltage is (using Eq. 4 in the second regime of operation, with $\tau_e \to \infty$ and $s_\Delta \to -\sigma_b$)

$$\tilde{v}_{sense\,reference}(t) = j\left[\frac{M_{be}M_{sb}}{R}\right]\sqrt{\frac{E_0}{2T_0}}\left[1 + \frac{\sigma_b}{s_b}\right]^2 s_b^2 e^{j\omega_b t}$$

$$\cong j\left[\frac{M_{be}M_{sb}}{R}\right]\sqrt{\frac{E_0}{2T_0}}\, s_b^2 e^{j\omega_b t}$$

In the reference case, an optimal coherent receiver matched to the marker will exhibit a signal-to-noise ratio (see below analysis) of:

$$SNR_{reference} \cong \left|\left[\frac{M_{be}M_{sb}}{R}\right] s_b^2\right|^2 \frac{E_0}{N_0}$$

Detector Characteristics Over Frequency

Detection of the marker signal in the pulsed case is restricted to the third regime of Eq. 4 to maintain (temporal) orthogonality with the excitation signal. The observation interval is thus no larger than $T_0 - \tau_e$. The sensed voltage for $t > \tau_e/2$ is:

$$\tilde{v}_{sense}(t) = \left[\frac{M_{be}M_{sb}}{R}\right]\sqrt{\frac{E_e}{2}}\, s_b^2 \sigma_b \hat{P}(s_b) e^{s_b t}$$

where $\hat{P}(s)$ is a Laplace transform of $\tilde{p}^*(t)$, properly normalized (see further detail below).

$$\hat{P}(s_b) = \frac{\int dt\, e^{s_b t}\tilde{p}*(t)}{[\int dt |\tilde{p}(t)|^2]^{1/2}}$$

For an arbitrary kernel $\tilde{k}(t)$, the signal-to-noise ratio of a coherent detector is $$SNR_{coherent} = \left|\left[\frac{M_{be}M_{sb}}{R}\right] s_b^2 \sigma_b \hat{P}(s_b)\right|^2 \frac{\left|\int dt\, e^{s_b t}\tilde{k}^*(t)\right|^2}{\int dt |\tilde{k}(t)|^2} \frac{E_e}{N_0}$$

$$= \left|\left[\frac{M_{be}M_{sb}}{R}\right] s_b^2\right|^2 |\sigma_b \hat{P}(s_b) \hat{K}(s_b)|^2 \frac{E_e}{N_0}$$

where the integration limits are understood to span the observation interval. Setting $E_e = E_0$ for constant excitation energy, the relative sensitivity of a coherent correlation receiver, denoted $\rho$, is thus given by [Eq. 5]:

$$\rho = \frac{SNR_{coherent}}{SNR_{reference}}$$

$$= |\sigma_b \hat{P}(s_b)\hat{K}(s_b)|^2$$

This result facilitates computation and highlights the contribution of the correlation kernel in tailoring the selectivity of the receiver.

EXAMPLE

Optimum Receiver for 100 kHz Marker, Q=40, 16 Cycle Pulse

The receiver observation interval is $\tau_e/2 < t < \infty$, where $\tau_e$ is sixteen cycles of the 100 kHz carrier. The normalized pulse and its corresponding Laplace transform are thus $$\tilde{p}(t) = -\frac{j}{\sqrt{\tau_e}} e^{j\omega_e t} \text{rect}(t/\tau_e)$$

$$\hat{P}(s_b) = \frac{j}{\sqrt{\tau_e}}\left[\frac{e^{s_\Delta \tau_e/2} - e^{-s_\Delta \tau_e/2}}{s_\Delta}\right]$$

The correlation kernel has a natural frequency:

$$s_r = -\sigma_r + j\omega_r$$

where $\omega_r = \omega_e = 2\pi \times 10^5$ and $\sigma_r = \sigma_b$. It is assumed that $\sigma_b$ is constant of all markers of interest. This implies that $\omega_b/Q$ is constant.

The optimum kernel for a 400 kHz marker and its corresponding Laplace transform are:

$$\tilde{k}(t) = \sqrt{2\sigma_r e^{\sigma_r \tau_e}} e^{s_r t} \mu(t - \tau_e/2)$$

$$\hat{K}(s_b) = -\sqrt{2\sigma_r e^{\sigma_r \tau_e}}\left[\frac{e^{(s_\Delta - \sigma_r)\tau_e/2}}{s_\Delta - \sigma_r}\right]$$

The relative sensitivity according to Eq. 5 is thus $$\rho = \frac{2\sigma_b^2 \sigma_r}{\tau_e}\left|\frac{1 - e^{s_\Delta \tau_e}}{s_\Delta(s_\Delta - \sigma_r)}\right|^2$$

The efficiency is determined by taking $s_\Delta \to -\sigma_b$, whence $$\eta = \frac{1}{2\sigma_b \tau_e}[1 - e^{-\sigma_b \tau_e}]^2$$

Figure 14:
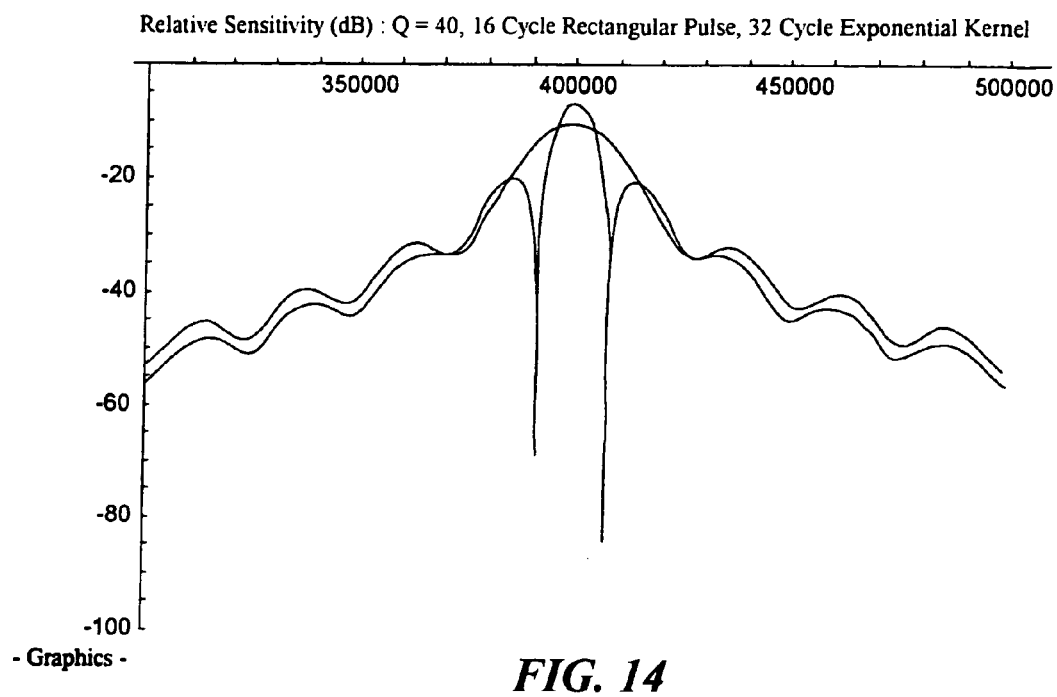
FIG. 14 is a graph of the relative sensitivity of a coherent detector for various parameters.

The efficiency is maximized for $\sigma_b \tau_e = 2\pi/5$, which justifies the selection of a 16 cycle pulse when Q is 40; in this case, the efficiency is −6.9 dB. A plot of the relative sensitivity over 300 kHz to 5000 kHz is shown in FIG. 14. For comparison, the relative sensitivity of an incoherent receiver is also plotted.

Maximizing Efficiency in the Constant Energy Case

When the measurement interval $T_0$ is finite, the observation interval can be denoted $\tau_o = T_0 - \tau_e$. For simplicity, as before, we assume no "dead zone" between the excitation and observation intervals. A one-cycle dead zone, which is expected in a practical system, will have a fraction of a dB penalty. Using an optimum correlation kernel, the maximum available efficiency becomes [Eq. 6]:

$$\eta = \frac{1}{2\sigma_b \tau_e}[1 - e^{-\sigma_b \tau_e}]^2 [1 - e^{-2\sigma_b \tau_o}]$$

Figure 15:
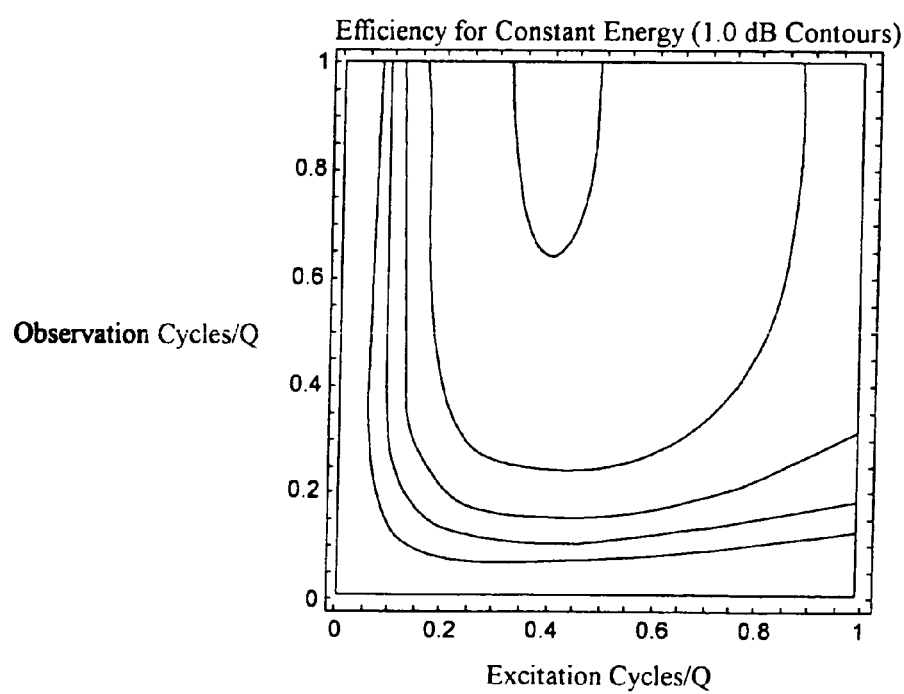
FIG. 15 is a graph of efficiency for a constant energy case.

Efficiency can be used as a criterion when specifying excitation and observation intervals in an operational system. As seen in FIG. 15, Eq. 6 can be plotted as a function of the excitation and observation intervals, in carrier cycles normalized by the marker Q (using $\sigma_b = \pi f_b/Q$).

In this case, efficiency is maximized for 0.4 Q excitation cycles, and an infinitely long observation interval (although 0.7 Q cycles of observation time is essentially optimum).

Case 2: Constant Amplitude

Setting $E_0 = A_0^2 T_0/2$ and $E_e = A_e^2 \tau_e/2$ in the SNR equations above, and setting $A_o = A_e$ yields the relative sensitivity:

$$\rho_{constant\ amplitude} = \frac{\tau_e}{T_0} \rho$$

whence the maximum available efficiency in this case is $$\eta_{constant\ amplitude} = \frac{1}{2\sigma_b(\tau_e + \tau_o)}[1 - e^{-\sigma_b \tau_e}]^2 [1 - e^{-2\sigma_b \tau_o}]$$

Figure 16:
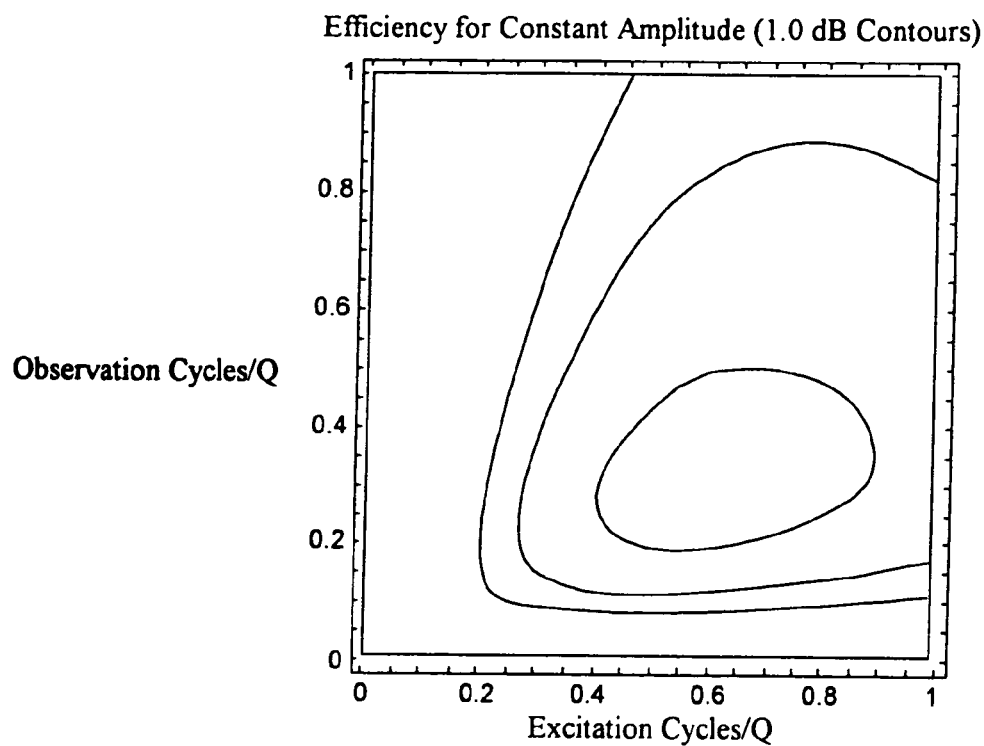
FIG. 16 is a graph of efficiency for a constant amplitude case.

Efficiency in this case is shown in FIG. 16.

Case 3: Marker Saturation

Using the model of saturation developed above, it is straightforward to show that, in this case:

$$SNR_{refrence} = \left|\left[\frac{M_{sb}}{R}\right]s_b\right|^2 \frac{|A_{sat}|^2 T_0}{2N_0}$$

$$SNR_{coherent} = \left|\left[\frac{M_{sb}}{R}\right]s_b\right|^2 |\hat{K}(s_b)|^2 \frac{|A_{sat}|^2}{2N_0}$$

The relative sensitivity is thus:

$$\rho_{saturation} = \frac{e^{\sigma_b \tau_e}}{T_0}|\hat{K}(s_b)|^2$$

Figure 17:
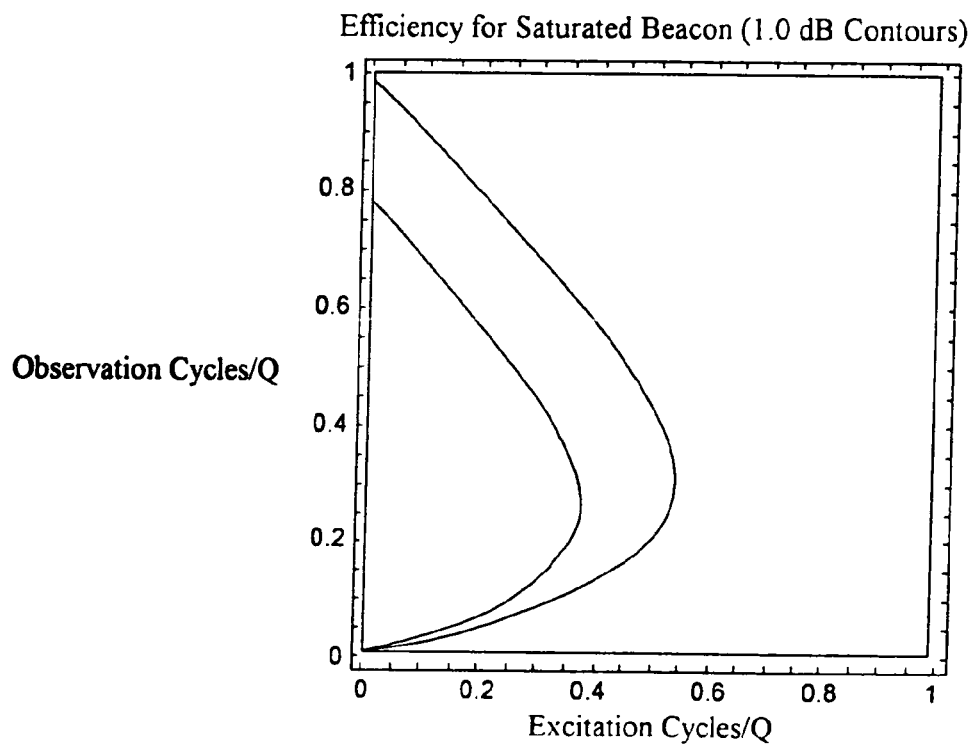
FIG. 17 is a graph of efficiency for a saturated marker case.

Thus, if all markers are excited to saturation, the only frequency selectivity is due to the correlation kernel. The maximum available efficiency (when the optimum kernel is used) in this case is $$\eta_{saturation} = \frac{1}{2\sigma_b(\tau_e + \tau_o)}[1 - e^{-2\sigma_b \tau_o}] \quad (8.1)$$

which is shown in FIG. 17. As seen, it is greatest for short excitation intervals, as the model used implicitly assumes the marker goes into saturation immediately upon excitation.

Maximizing Efficiency: Periodic Pulses

Expressions for efficiency have been described for three different cases, but each in the context of a single excitation pulse. These results can be extended to the case of periodic excitation.

Consider N sequential measurement intervals, where the results of N observations are integrated prior to calculating the detected output and assuming that any residual marker response from earlier intervals can be neglected. In a white noise environment, the signal-to-noise will be proportional to N. However, the SNR for the CW reference cases used in the efficiency calculations likewise scales as N, so the efficiency remains constant. Hence FIGS. 15, 16, and 17 can be used for design guidance when specifying the measurement timing of the system. The first case, constant energy, probably best matches the operational constraints of a practical system, whence the excitation interval should be in the range of 0.3–0.5 Q cycles and the observation interval about 0.6–1.0 Q cycles. Given the likelihood of marker saturation, the excitation interval should be biased towards the low side.

On the Use of Windows for Frequency Selectivity

In the description above, the correlation kernels were chosen to maximize the signal-to-noise ratio, and hence the efficiency. Within this framework, optimum choices for excitation and observation intervals were developed for the single pulse and periodic pulse cases.

However, optimum kernels are optimum only in the sense of maximizing the signal-to-noise ratio in a white noise environment. In an environment consisting of multiple markers, at multiple frequencies, use of alternate kernels permits the tailoring of the selectivity of the receiver. Indeed, in the extreme case of all markers being driven to saturation, selectivity is a function of the kernel alone.

Figure 18:
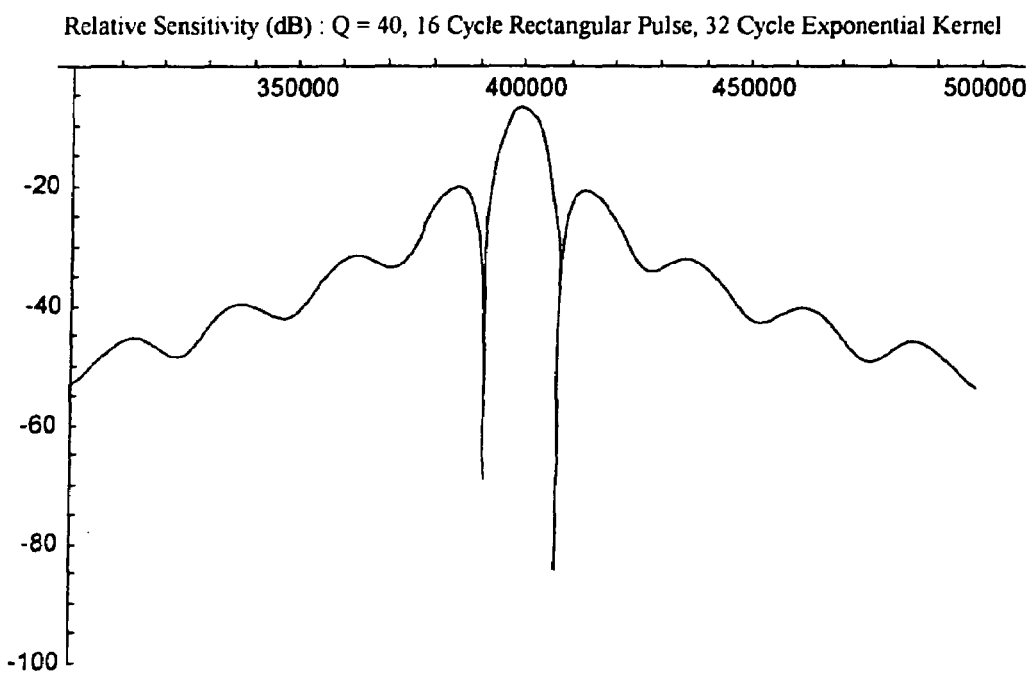
FIG. 18 is a graph of efficiency using a thirty-two cycle rectangular window.
Figure 19:
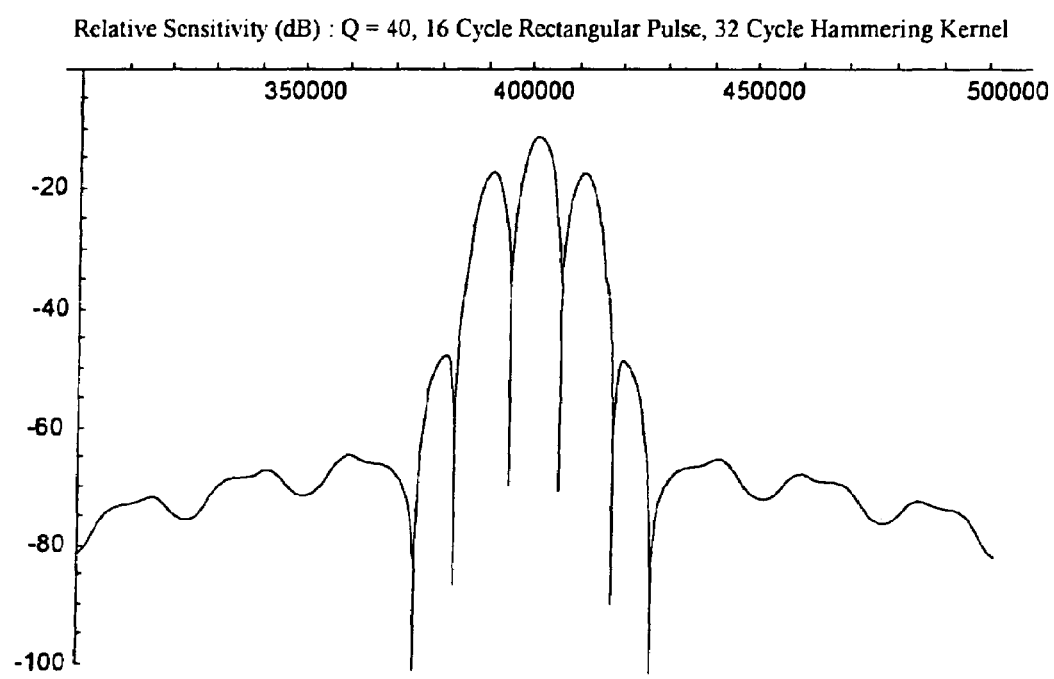
FIG. 19 is a graph of efficiency using a thirty-two cycle Hamming window.
Figure 20:
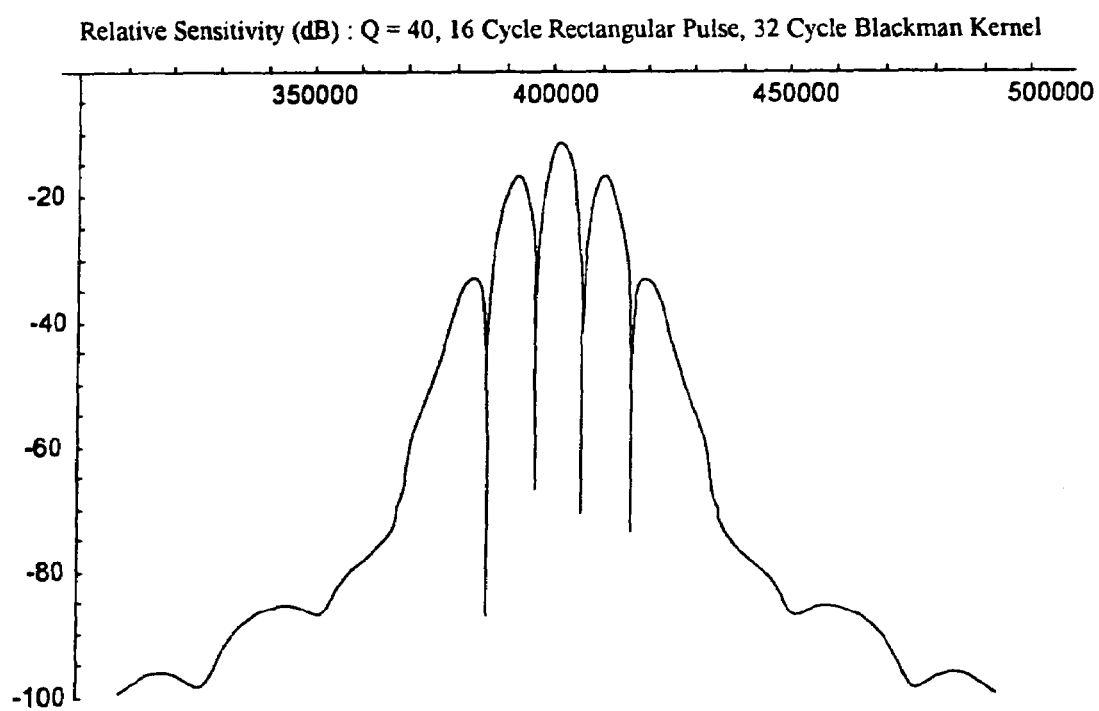
FIG. 20 is a graph of efficiency using a thirty-two cycle Blackman window.

The nature of the relative sensitivity function ($\rho$) suggests the use of windows to control the frequency characteristics of the kernel. FIGS. 18–20 show the effects of this. In all three cases, the excitation pulse is 16 cycles, and the marker Q is 40. It is assumed that the linear system model applies. The plots can be compared to FIG. 14 in which the optimum kernel is used.

The first case (FIG. 18) uses a rectangular kernel of 32 cycles; it is similar to the optimum case, but exhibits a slight loss of sensitivity (efficiency) at center frequency.

The second case (FIG. 19) uses a Hamming weighted kernel of 32 cycles; it exhibits somewhat more loss of sensitivity at center frequency, but the selectivity is substantially improved.

The third case (FIG. 20) uses a Blackman weighted kernel of 32 cycles. The sensitivity is degraded by about 6.5 dB from the first case.

Locating the Marker Using Receiver Outputs

As noted above, in one embodiment, the sensing array has thirty-two sensing coils 302. After the receiver 208 has completed the signal processing detailed above, the resulting output of the receiver 208 is thirty-two "cleaned up" digital output signals. These digital output signals may then be used to locate the marker. As detailed in my co-pending U.S. patent application Ser. No. 10/679,801 filed Oct. 6, 2003 entitled "Method and System for Marker Localization", each digital output signal is a measurement of one component of the magnetic field integrated over the aperture of the sensor array. The location system determines the location of the marker (i.e., marker location) from a set or array of measurements taken from the sensors (i.e., set of actual measurements). The location system compares the set of actual measurements to sets of reference measurements for various known locations within a bounding volume (also referred to as a localization volume). The bounding volume delimits the three-dimensional area in which the marker can be localized. A reference measurement for a known location indicates the measurements to be expected from the sensors when the marker is located at that known location.

Based on the comparisons, the location system identifies the set of reference measurements that most closely matches the set of actual measurements. The known location of the identified set of reference measurements represents the known location that is closest to the marker location, which is referred to as the "closest known location." The location system then uses sets of reference measurements for known locations near the closest known location to more accurately determine the marker location when it is not actually at one of the known locations.

In one embodiment, the location system determines the marker location based on an interpolation of a set of calculated measurements from the sets of reference measurements of known locations near the closest known location. Thus, the location system uses the set of reference measurements to find a known location that is close to the marker location to an accuracy that is dependent on the spacing of the known locations. The location system then uses an interpolation of sets of reference measurements at known locations near the closest known location to more accurately identify the marker location at a location between the known locations.

Multiple Markers

In the description above, for simplicity and clarity, it is assumed that a single marker is being located or sensed. In some applications, multiple markers are associated with a subject or patient. In such a case, the teachings herein can easily be extended to multiple markers. For example, each marker may be excited at resonance individually in a serial fashion and located sequentially. Thus, the use of multiple markers is contemplated by the present claimed invention.

Conclusion

Unless the context clearly requires otherwise, throughout the description and the claims, the words "comprise," "comprising," and the like are to be construed in an inclusive sense as opposed to an exclusive or exhaustive sense, that is to say, in the sense of "including, but not limited to." Words using the singular or plural number also include the plural or singular number, respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list, and any combination of the items in the list.

The above detailed descriptions of embodiments of the invention are not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, an array of hexagonally shaped sense coils may be formed on a planar array curved along at least one line to form a concave structure. Alternatively, the arrangement of coils on the panel may form patterns besides the "cross" pattern shown in FIGS. 3A and 3B. The coils may be arranged on two or more panels or substrates, rather than the single panel described herein. The teachings of the invention provided herein can be applied to other systems, not necessarily the system employing wireless, implantable resonating targets described in detail herein. These and other changes can be made to the invention in light of the detailed description.

The elements and acts of the various embodiments described above can be combined to provide further embodiments. All of the above U.S. patents and applications and other references are incorporated herein by reference. Aspects of the invention can be modified, if necessary, to employ the systems, functions and concepts of the various references described above to provide yet further embodiments of the invention.

These and other changes can be made to the invention in light of the above detailed description. In general, the terms used in the following claims should not be construed to limit the invention to the specific embodiments disclosed in the specification, unless the above detailed description explicitly defines such terms. Accordingly, the actual scope of the invention encompasses the disclosed embodiments and all equivalent ways of practicing or implementing the invention under the claims.

One skilled in the art will appreciate that although specific embodiments of the location system have been described herein for purposes of illustration, various modifications may be made without deviating from the spirit and scope of the invention. Accordingly, the invention is not limited except by the appended claims.

We claim:

1. A system for locating a marker associated with a patient comprising:
    an excitation source for emitting a series of exciting pulses, each exciting pulse emitted during an excitation interval, said exciting pulse causing said marker to resonate;
    a sensing array including a plurality of sensing coils, said sensing coils adapted for sensing a resonance signal of said marker and outputting a plurality of inputs during a observation interval that occurs following said excitation interval; and
    a receiver for analyzing said plurality of inputs to remove noise from said plurality of inputs, said receiver acting on said plurality of inputs provided during said observation interval,
    wherein said exciting pulses are emitted in a non-periodic manner.

2. The system of claim 1 further including a dithering circuit to introduce a pseudo-random dither into the timing of the start of said exciting pulses.

3. The system of claim 2 wherein said dither is approximately one-cycle of the resonant frequency of said marker.

4. A system for locating a marker associated with a patient comprising:
    means for emitting a series of exciting pulses, each exciting pulse emitted during an excitation interval, said exciting pulse causing said marker to resonate;
    means for sensing including a plurality of sensing coils, said sensing coils adapted for sensing a resonance signal of said marker and outputting a plurality of inputs during a observation interval that occurs following said excitation interval; and
    means for receiving and analyzing said plurality of inputs to remove noise from said plurality of inputs, said means for receiving and analyzing acting on said plurality of inputs provided during said observation interval,
    wherein said exciting pulses are emitted in a non-periodic manner.

5. The system of claim 4 further including means for dithering operative to introduce a pseudo-random dither into the timing of the start of said exciting pulses.

6. The system of claim 5 wherein said dither is approximately one-cycle of the resonant frequency of said marker.

7. A method for locating a marker associated with a patient comprising:
provinding an excitation source for emitting a series of exciting pulses, each exciting pulse emitted during an excitation interval, said exciting pulse causing said marker to resonate;
providing a sensing array including a plurality of sensing coils, said sensing coils adapted for sensing a resonance signal of said marker and outputting a plurality of inputs during a observation interval that occurs following said excitation interval; and
providing a receiver for analyzing said plurality of inputs to remove noise from said plurality of inputs, said receiver acting on said plurality of inputs provided during said observation interval,
wherein said exciting pulses are emitted in a non-periodic manner.

8. The method of claim 7 further including introducing a pseudo-random dither into the timing of the start of said exciting pulses.

9. The system of claim 8 wherein said dither is approximately one-cycle of the resonant frequency of said marker.

10. A system for locating a marker associated with a patient comprising:
an excitation source for emitting a series of exciting pulses, each exciting pulse emitted during an excitation interval, said exciting pulse causing said marker to resonate;
a sensing array including a plurality of sensing coils, said sensing coils adapted for sensing a resonance signal of said marker and outputting a plurality of inputs during a observation interval that occurs following said excitation interval; and
a receiver for analyzing said plurality of inputs to remove noise from said plurality of inputs, said receiver acting on said plurality of inputs provided during said observation interval,
wherein said exciting pulses have a random starting polarity.

11. A method for locating a marker associated with a patient comprising:
providing an excitation source for emitting a series of exciting pulses, each exciting pulse emitted during an excitation interval, said exciting pulse causing said marker to resonate;
providing a sensing array including a plurality of sensing coils, said sensing coils adapted for sensing a resonance signal of said marker and outputting a plurality of inputs during a observation interval that occurs following said excitation interval; and
providing a receiver for analyzing said plurality of inputs to remove noise from said plurality of inputs, said receiver acting on said plurality of inputs provided during said observation interval,
wherein said exciting pulses have a random starting polarity.

12. A system for locating a marker associated with a patient comprising:
an excitation source for emitting a series of exciting pulses, each exciting pulse emitted during an excitation interval, said exciting pulse causing said marker to resonate;
a sensing array including a plurality of sensing coils, said sensing coils adapted for sensing a resonance signal of said marker and outputting a plurality of inputs during a observation interval that occurs following said excitation interval; and
a receiver for analyzing said plurality of inputs to remove noise from said plurality of inputs, said receiver acting on said plurality of inputs provided during said observation interval,
wherein said exciting pulses have a random starting phase.

13. A method for locating a marker associated with a patient comprising:
providing an excitation source for emitting a series of exciting pulses, each exciting pulse emitted during an excitation interval, said exciting pulse causing said marker to resonate;
providing a sensing array including a plurality of sensing coils, said sensing coils adapted for sensing a resonance signal of said marker and outputting a plurality of inputs during a observation interval that occurs following said excitation interval; and
providing a receiver for analyzing said plurality of inputs to remove noise from said plurality of inputs, said receiver acting on said plurality of inputs provided during said observation interval,
wherein said exciting pulses have a random starting phase.

* * * * *